US009638630B2

(12) United States Patent
Eddy et al.

(10) Patent No.: US 9,638,630 B2
(45) Date of Patent: May 2, 2017

(54) METHODS AND DEVICES FOR ANALYZING GASES IN WELL-RELATED FLUIDS USING FOURIER TRANSFORM INFRARED (FTIR) SPECTROSCOPY

(71) Applicant: TOTAL Gas Detection Ltd., Calgary (CA)

(72) Inventors: Michael A. Eddy, Calgary, CA (US); Frederick G. Haibach, Wilbraham, MA (US); Erik R. Deutsch, Brookline, MA (US)

(73) Assignee: TOTAL GAS DETECTION LTD., Calgary (CA)

( * ) Notice: Subject to any disclaimer, the term of this patent is extended or adjusted under 35 U.S.C. 154(b) by 52 days.

(21) Appl. No.: 14/086,764

(22) Filed: Nov. 21, 2013

(65) Prior Publication Data
US 2015/0136961 A1  May 21, 2015

(51) Int. Cl.
*G01N 21/3504* (2014.01)
*G01N 21/03* (2006.01)
(Continued)

(52) U.S. Cl.
CPC ..... *G01N 21/3504* (2013.01); *G01N 21/0332* (2013.01); *E21B 49/005* (2013.01); *G01N 2021/3595* (2013.01)

(58) Field of Classification Search
CPC ............ G01N 21/35; G01N 2021/3595; E21B 49/005
(Continued)

(56) References Cited

U.S. PATENT DOCUMENTS 3,593,023 A * 7/1971 Dodson ............... G01M 15/108
250/343
4,635,735 A * 1/1987 Crownover ............. E21B 49/08
175/42
(Continued)

FOREIGN PATENT DOCUMENTS

CA  2718816  9/2009
CA  2719816  12/2009
(Continued)

OTHER PUBLICATIONS

Ablard, P. et al., The Expanding Role of Mud Logging, Oilfield Review, Spring 2012: 24 No. 1.
(Continued)

*Primary Examiner* — David Porta
*Assistant Examiner* — Gisselle Gutierrez
(74) *Attorney, Agent, or Firm* — Norton Rose Fulbright US LLP

(57) ABSTRACT

Devices, assemblies, systems and methods useful in the detection of hydrocarbons in well-related fluids such as drilling fluids during well-related operations are disclosed. Such devices, assemblies, systems and methods may be used for real-time analysis of gas(es) extracted from a fluid associated with an ongoing well-related operation. An exemplary method may comprise: receiving gas extracted from the fluid associated with the well-related operation; analyzing the gas using Fourier Transform Infrared (FTIR) spectroscopy; and generating one or more signals useful in the determination of a composition of the gas extracted from the fluid.

17 Claims, 23 Drawing Sheets

(51) Int. Cl.
*G01N 21/35* (2014.01)
*E21B 49/00* (2006.01)

(58) Field of Classification Search
USPC ................................................ 250/255, 262
See application file for complete search history.

(56) References Cited

U.S. PATENT DOCUMENTS

| | | | | |
|---|---|---|---|---|
| 4,824,790 | A * | 4/1989 | Carangelo | G01N 5/04 422/80 |
| 5,199,509 | A | 4/1993 | Wright et al. | 175/50 |
| 6,666,099 | B2 * | 12/2003 | Taylor | G01N 33/2823 73/863.12 |
| 7,884,937 | B2 | 2/2011 | Prasad et al. | 356/437 |
| 8,884,215 | B2 * | 11/2014 | Gunn | G01N 33/2823 250/253 |
| 2007/0180676 | A1 * | 8/2007 | Hwang | H01L 21/681 29/407.01 |
| 2009/0122383 | A1 | 5/2009 | Reyes et al. | 359/238 |
| 2009/0227287 | A1 | 9/2009 | Kotidis | 455/556.1 |
| 2009/0285721 | A1 | 11/2009 | DeGreeve et al. | 422/82.09 |
| 2010/0027004 | A1 | 2/2010 | Bonyuet et al. | 356/326 |
| 2010/0282959 | A1 | 11/2010 | Dong et al. | 250/269.1 |
| 2010/0302546 | A1 * | 12/2010 | Azimi | G01J 3/02 356/437 |
| 2011/0063619 | A1 | 3/2011 | Schildkraut et al. | 356/452 |
| 2011/0308391 | A1 | 12/2011 | DeGreeve et al. | 95/260 |
| 2011/0313670 | A1 | 12/2011 | DeGreeve et al. | 702/13 |
| 2012/0033220 | A1 | 2/2012 | Kotidis et al. | 356/445 |
| 2012/0200855 | A1 | 8/2012 | Bonyuet et al. | 356/418 |
| 2013/0017644 | A1 * | 1/2013 | Carter, III | C23C 16/4405 438/57 |

FOREIGN PATENT DOCUMENTS

| | | | | |
|---|---|---|---|---|
| EP | 706042 | A1 * | 4/1996 | G01N 21/35 |
| RU | 2441219 | | 7/2012 | |

OTHER PUBLICATIONS

Block Engineering, Lasertune Mid-IR QCL Source Description, 2013.
Block Engineering, M90/M100 Spectrometer Description, 2010.
Block Engineering, Michelson Interferometer Operation, 2013.
Block Engineering, MINI-FT Interferometer/Detector Module Description, 2013.
Genia Photonics, Mid IR Spectroscopy Description, http://www.geniaphotonics.com/business-markets/industrial/i-mid-ir-spectroscopy/, accessed Aug. 11, 2012.
Klingbeil, A. et al., Temperature-dependent mid-IR absorption spectra of gaseous hydrocarbons. Journal of Quantitative Spectroscopy and Radiative Transfer, vol. 107; issue 3; Oct. 2007; 407-420.
Pason, The Pason Gas Analyzer: The chromatograph Advantage, Product Application Note, Revised Oct. 28, 2011.
Roberts, J., Key System Parameters for Fourier Transform-InfraRed Analysis of Industrial Gases. Gases & Instrumentation, Nov./Dec. 2012: 11.
Wikipedia, Fourier transform infrared spectroscopy, Oct. 25, 2013, http://en.wikipedia.org/wiki/Fourier_transform_infrared_spectroscopy.

* cited by examiner

METHODS AND DEVICES FOR ANALYZING GASES IN WELL-RELATED FLUIDS USING FOURIER TRANSFORM INFRARED (FTIR) SPECTROSCOPY

TECHNICAL FIELD

The disclosure relates generally to oil and gas wells, and more particularly to the detection of hydrocarbons in well-related fluids.

BACKGROUND OF THE ART

Drilling oil and gas wells can include the use of drilling fluid such as "drilling mud" which is pumped down the drill string to circulate from the drilling head and carry upward to the surface the debris created by the drilling operation. When a gas-containing strata is encountered by the drilling operation, a certain amount of the gas from the strata can be entrained in the drilling mud and thus be carried to the surface. Extracting these gases from the drilling mud allows determination of the presence of hydrocarbons and an estimate of the quantity of hydrocarbon being encountered. Analysis of the recovered gas can be used to make a determination as to the desirability of recovering the gas or oil from the particular strata. This practice is also known as "mud logging".

Some devices for conducting analysis on the recovered gas for mud logging activities exist. However, existing devices can be relatively difficult to manufacture and require individual calibration. Some existing devices also have narrow operating ranges that limit the number of hydrocarbons that may be detected and also have limited accuracy and repeatability.

Improvement is therefore desirable.

SUMMARY

The present disclosure discloses devices, assemblies, systems and methods relating to the identification of substances of interest in well-related fluids during operations relating to oil and gas wells.

In one aspect, the disclosure describes a method for real-time analysis of gas extracted from a fluid associated with an ongoing well-related operation. The method comprises:
  receiving gas extracted from the fluid associated with the well-related operation;
  analyzing the gas using Fourier Transform Infrared (FTIR) spectroscopy; and
  generating one or more signals useful in the determination of a composition of the gas extracted from the fluid.

In another aspect, the disclosure describes a method for identification of hydrocarbons in a fluid associated with a well-related operation. The method comprises:
  extracting gas from the fluid associated with the well-related operation;
  analyzing the gas using Fourier Transform Infrared (FTIR) spectroscopy; and
  generating one or more signals useful in the identification of hydrocarbons in the gas extracted from the fluid.

In another aspect, the disclosure describes a system comprising:
  a reservoir configured to hold a fluid associated with a well-related operation;
  a gas extractor configured to cause the release of gas from the fluid in the reservoir; and
  a device configured to conduct Fourier Transform Infrared (FTIR) spectroscopy on the extracted gas, the device comprising an inlet in fluid communication with the gas extractor.

In another aspect, the disclosure describes a device for conducting Fourier Transform Infrared (FTIR) spectroscopy of gas extracted from a fluid associated with a well-related operation. The device comprises:
  a gas cell having an inlet for receiving gas extracted from the fluid;
  a pump configured to induce flow of the extracted gas through the gas cell;
  a radiation source for directing radiation through the gas cell;
  an interferometer configured to interact with the radiation;
  a detector configured to measure a radiation output from the interferometer and generate one or more signals representative of radiation intensity;
  a processor; and
  a medium comprising machine-readable instructions executable by the at least one processor and configured to cause the processor to generate, based on the signals generated by the detector, data useful in the determination of a composition of the extracted gas.

In another aspect, the disclosure describes a device for conducting Fourier Transform Infrared (FTIR) spectroscopy. The device comprises:
  a gas cell;
  a radiation source for directing radiation through the gas cell;
  a thermal conductor thermally coupled between the gas cell and the radiation source for transferring heat from the radiation source to the gas cell by conduction;
  an interferometer configured to interact with the radiation;
  a detector configured to measure a radiation output from the interferometer and generate one or more signals representative of radiation intensity;
  a processor; and
  a medium comprising machine-readable instructions executable by the at least one processor and configured to cause the processor to generate, based on the signals generated by the detector, data useful in the determination of a composition of a gas in the gas cell.

In another aspect, the disclosure describes a device for conducting Fourier Transform Infrared (FTIR) spectroscopy. The device comprises:
  a gas cell comprising a first interface configured to removably receive a first window;
  a radiation source for directing radiation through the first removable window;
  an interferometer configured to interact with the radiation;
  a detector configured to measure a radiation output from the interferometer and generate one or more signals representative of radiation intensity;
  a processor; and
  a medium comprising machine-readable instructions executable by the at least one processor and configured to cause the processor to generate, based on the signals generated by the detector, data useful in the determination of a composition of a gas in the gas cell.

In another aspect, the disclosure describes a gas cell for use in spectroscopy. The gas cell comprises:
  a body defining a cavity for holding a gas to be analyzed by spectroscopy;
  a first widow configured to permit radiation into the cavity, the first window being removably secured to the body; and a second window configured to permit radiation out of the cavity, the second window being removably secured to the body.

In another aspect, the disclosure describes a method for servicing a gas cell for use in spectroscopy where the gas cell comprises a body having a cavity and a removable window to the cavity configured to permit passage of radiation. The method comprises:
  removing the window from the body; and
  one of:
    cleaning the window and installing the cleaned window with the body; and
    installing a replacement window with the body.

In another aspect, the disclosure describes a method for calibrating a gas cell for use in spectroscopy. The method comprises:
  evacuating the gas cell and creating a vacuum condition inside the gas cell;
  directing radiation through the gas cell; and
  measuring radiation exiting the gas cell while the cell is under the vacuum condition.

In another aspect, the disclosure describes a method for heating a gas cell in a device configured to conduct Fourier Transform Infrared (FTIR) spectroscopy where the device comprises a source of radiation. The method comprises:
  operating the source of radiation; and
  transferring heat from the source to the gas cell by conduction.

In another aspect, the disclosure describes a method for real-time analysis of gas extracted from a fluid associated with an ongoing well-related operation. The method may comprise:
  receiving gas extracted from the fluid associated with the well-related operation;
  analyzing the gas using spectroscopy using wavelengths in the mid infrared range; and
  generating one or more signals useful in the determination of a composition of the gas extracted from the fluid.

In another aspect, the disclosure describes the use of Fourier Transform Infrared (FTIR) spectroscopy during a well-related operation.

In a further aspect, the disclosure describes the use of Fourier Transform Infrared (FTIR) spectroscopy for detecting hydrocarbons in gas extracted from drilling fluid during a mud logging operation.

Further details of these and other aspects of the subject matter of this application will be apparent from the detailed description and drawings included below.

DESCRIPTION OF THE DRAWINGS

Reference is now made to the accompanying drawings, in which.

DETAILED DESCRIPTION

Aspects of various embodiments are described through reference to the drawings.

The present disclosure relates generally to oil and gas wells but the devices, assemblies, systems and methods disclosed herein may also be used in other applications. In particular, the devices, assemblies, systems and methods disclosed herein may be useful in the detection of hydrocarbons in well-related fluids during well-related operations. For example, the devices, assemblies, systems and methods disclosed herein may be useful in obtaining the concentration(s) of one or more hydrocarbons found in gas(es) extracted from well-related fluid(s). Such well-related fluids may, for example, include drilling fluid(s) circulated through a well during a drilling operation. Liquid drilling fluid may also be called "drilling mud". The terms "well-related fluid" and "drilling fluid" are intended to encompass fluid(s) in various forms and may include water-based muds (which can be dispersed or non-dispersed), non-aqueous muds, usually called oil-based muds, and gaseous drilling fluids, in which a wide range of gases can be used. Drilling fluids may be in gaseous form, liquid form and/or may comprise foams. Specific examples of drilling fluids may include one or more of air, air/water mixture, air/polymer mixture, water, water-based mud, oil-based mud and synthetic-based fluids. Such different types of drilling fluids may be selected based on different applications and process parameters. One or more additives such as foaming agents may also be added to such drilling fluids in some applications.

Exemplary functions of drilling fluids may include providing hydrostatic pressure to prevent formation fluids from entering into the well bore, keeping the drill bit cool and clean during drilling, carrying out drill cuttings, and suspending the drill cuttings while drilling is paused and when the drilling assembly is brought in and out of the hole. The specific type and composition of drilling fluid(s) used for a particular task may be selected to substantially avoid formation damage and to limit corrosion.

The devices, assemblies, systems and methods disclosed herein may be useful in mud logging activities associated with well-related operations. For example, the devices, assemblies, systems and methods disclosed herein may be useful during drilling of wells, geosteering of wells and/or hydraulically/multistage fracturing of wells based on information obtained during such mud logging activities. The information may also be used to make decisions about areas in which to drill, expand or cancel existing drilling programs. The devices, assemblies, systems and methods disclosed herein may be used while one or more well-related activities is/are ongoing. For example, the devices, assemblies, systems and methods disclosed herein may be useful for measurement-while-drilling (MWD) and logging-while-drilling (LWD) activities, and, in various embodiments, may be considered MWD and/or LWD tools.

Figure 1:
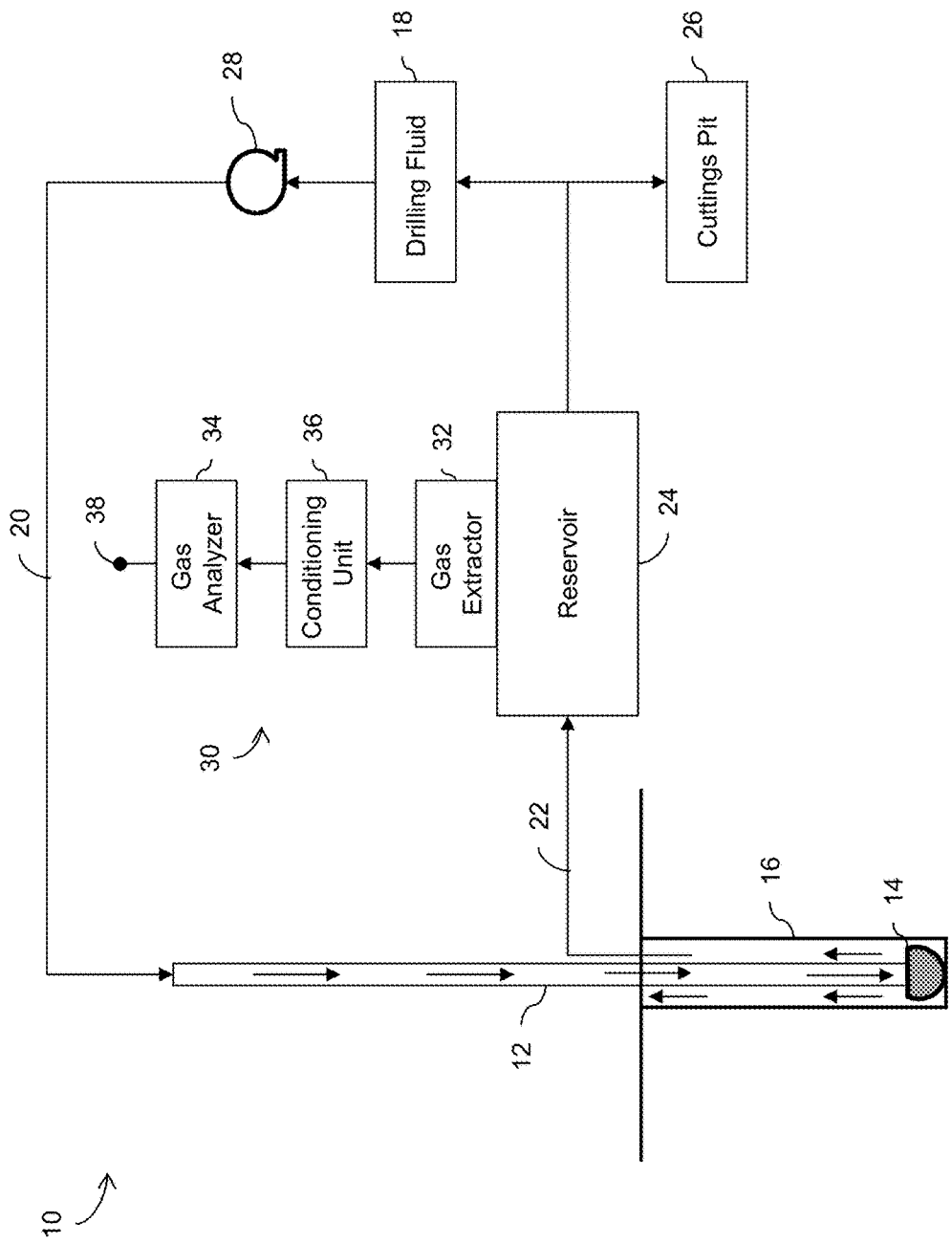
FIG. 1 is a schematic representation of an exemplary well-drilling installation.

FIG. 1 schematically illustrates an exemplary installation, generally shown at 10, for conducting an operation associated with an oil and/or gas well and which may involve well-related fluid(s) (e.g., drilling fluid(s)). For example, installation 10 may be configured for conducting operations related to exploring, developing and/or completing oil and gas wells. In various embodiments, installation 10 may be configured for conducting well-drilling (i.e., may comprise or be part of a drilling rig) and may make use of well-related fluids such as drilling fluid(s).

Installation 10 may comprise drill pipe 12 and drill head 14 mounted to drill pipe 12 and used to drill oil and/or gas well bore 16. Drill head 14 may comprise a conventional or other type of drill bit(s) (e.g., cutter(s)) or other device(s) configured for drilling with air and/or foam. During operation of drill pipe 12 and drill head 14, drilling fluid(s) 18 such as drilling mud, foam and/or air, for example, may be pumped through drill pipe 12 down into well bore 16, through jets (not shown) in drill head 14 and back up the annulus formed between drill pipe 12 and well bore 16. Drilling fluid 18 may be used to cool drill head 14 and bring cuttings and gases along with it and out of well bore 16. The flow of drilling fluid 18, such as drilling mud, into drill pipe 12 and out of well bore 16 is illustrated by the arrows in FIG. 1. Drilling fluid 18 may be delivered to drill pipe 12 via delivery line 20 and returned from well bore 16 via return line 22. Delivery line 20 may comprise a hose, also known as a "Kelly hose" or "mud hose", which may be a relatively flexible, steel reinforced, high pressure hose that connects to drill pipe 12 while also permitting free vertical movement of drill pipe 12 and facilitating the flow of drilling fluid 18 to drill pipe 12.

Installation 10 may also comprise reservoir 24 for receiving drilling fluid 18 returning from well bore 16 via return line 22. Reservoir 24 may comprise a metallic container open to the atmosphere. Reservoir 24 may be used to slow the flow of drilling fluid 18 after it has gained momentum from being circulated down and up well bore 16. Reservoir 24 may be of the type known as "possum belly" may also be referred to as a distribution box or flowline trap. In addition or alternatively, reservoir 24 may comprise means for separating cuttings (i.e., solids) from drilling fluid 18 prior to recycling drilling fluid 18. For example, reservoir 24 may comprise such means known as "shale shaker" for separating cuttings (e.g., solids) from drilling fluid 18. The separation of cuttings from drilling fluid 18 may be conducted using one or more vibrating screens through which drilling fluid 18 and particles smaller than a predetermined size may fall through the screen(s) and particles larger than the predetermined size may remain on top of the screen(s) and then directed to cuttings pit 26. A possum belly may be used to contain drilling fluid 18 as it is pumped out of the flow line before spilling onto the shaker screen.

In various embodiments, reservoir 24 may comprise any suitable container configured to contain drilling fluid 18 being returned from well bore 16 during a well-related operation. For example, reservoir 24 may be configured to contain a supply of circulating drilling fluid 18 that is used during drilling or other well-related operation. Drilling fluid 18, out of which some cuttings may have been removed, may then be re-directed to drill pipe 12 via pump 28 and delivery line 20. Pump 28 may be used to pressurize drilling fluid 18 to a pressure selected to achieve a desired flow velocity in the annulus between drill pipe 12 and well bore 16 in order to entrain a desired amount and size of cuttings out of well bore 16.

In addition to cuttings, the flow of drilling fluid 18 returning from well bore 16 through return line 22 and into reservoir 24 may also contain gas(es) that drill head 14 has encountered while drilling well bore 16. Accordingly, one or more mud logging units (not shown) may be used to analyze the contents of the drilling fluid 18 returned from well bore 16 to determine various characteristics of well bore 16 including the likelihood of the well being drilled will produce a significant amount of oil and/or gas. For example, the presence of one or more hydrocarbons such as methane, ethane, propane, butane, pentane, hexane, heptane and octane in drilling fluid 18 returned from well bore 16 may provide an indication that well bore 16 will produce oil and/or gas. The analysis of drilling fluid 18 may also be used to control at least some aspect of the drilling being carried out by installation 10. Accordingly, results from the analysis of drilling fluid 18 may be used as a basis for controlling drilling and/or other well-related operation(s).

Installation 10 may comprise means for detecting one or more hydrocarbons such as methane, ethane, propane, butane, pentane, hexane, heptane and/or octane in drilling fluid 18 returning from well bore 16. In various embodiments, installation 10 may comprise one or more devices or systems for detecting one or more hydrocarbons and/or other substances. Such devices or systems may, for example, be configured to conduct spectroscopy on one or more gases extracted from drilling fluid 18 returning from well. For example, installation 10 may comprise system 30, which may include reservoir 24, gas extractor 32 and gas analyzer 34. Gas extractor 32 may be any suitable known or other device to extract gaseous fluid(s) from drilling fluid 18. For example gas extractor 32 may comprise a gas agitator that draws drilling fluid 18 from the bottom of reservoir 24, agitates drilling fluid 18 and captures gas(es) coming out of drilling fluid 18 due to the agitation. Gas(es) extracted by gas extractor 32 may be directed to gas analyzer 34 via suitable conduit(s) for analysis. Gas analyzer 34 may be substantially standalone with only needing a source of electricity for powering various component of gas analyzer 34 as described below. It should be understood that, depending on the type of application and/or drilling fluid used, a different type of gas extractor 32 may be used. For example, in the case of air or other gaseous substance being used as drilling fluid 18, gas extractor 32 as shown herein may not be required and the detection of hydrocarbon(s) may be conducted on fluid (i.e., gas(es)) returning in a blooey line. Accordingly, gas(es) may be extracted (e.g., drawn, released) from the blooey line for the purpose of being directed to gas analyzer 34.

The gas(es) directed to gas analyzer 34 may include ambient air and moisture since system 30 may not be completely sealed from the atmosphere. Accordingly, prior to directing the gas(es) to gas analyzer 34, the gas(es) may be treated (e.g., conditioned) by conditioning unit 36. Conditioning unit 36 may comprise any suitable means of treating the gas(es) prior to analysis by gas analyzer 34. In various embodiments, conditioning unit 36 may comprise a gas dryer that may remove at least some moisture (i.e., water) that may be present in the extracted gas(es). It should be understood that drying and/or other conditioning of the extracted gas(es) may be used depending on the nature of the well-related fluid (e.g., drilling fluid 18) in question, the process and/or environment conditions and also depending on the type of analysis conducted on the extracted gas(es).

As explained further below, gas analyzer 34 may be configured to conduct Fourier Transform Infrared (FTIR) spectroscopy. FTIR is a technique which may be used to obtain an infrared spectrum of absorption, emission, photoconductivity or Raman scattering of a solid, liquid or gas. Gas analyzer 34 may be configured to simultaneously collect spectral data in a wide spectral range. In various embodiments, gas analyzer 34 may be configured to use one or more wavelengths in the mid infrared range such as between about 5 μm and about 13.5 μm, for example. It should be understood that the one or more wavelengths may be selected based on the constituents (e.g., hydrocarbons) of the extracted gas(es) to be detected. For example, a range of wavelengths for spectroscopy may be selected to include one or more atomic transitions (e.g., absorbance peak, emission peak, etc.) or other spectroscopic characteristic(s) associated with one or more of the constituents to be detected. For example, wavelengths in the mid infrared range may be selected because of absorbance peaks found within this range for at least some hydrocarbons. In various embodiments, the range of wavelengths may be selected so that one or more of methane, ethane, propane, butane and pentane (i.e., hydrocarbons C1 to C5) exhibit distinguishable absorbance peaks or other spectroscopic characteristic(s) within that range in order to facilitate the identification of those constituents. In various embodiments, the range of wavelengths may be selected so that one or more of methane, ethane, propane, butane, pentane, hexane, heptane and octane (i.e., hydrocarbons C1 to C8) exhibit distinguishable absorbance peaks or other spectroscopic characteristic(s) within that range. Since the spectroscopic characteristics of substances may vary with variances in temperature and/or pressure, the wavelength range may also be selected based on expected temperatures and pressures of the extracted gas(es) when inside gas analyzer 34 during operation of gas analyzer 34.

Gas analyzer 34 may be configured to generate one or more signals useful in the determination of a composition of the gas extracted from drilling fluid 18. Gas analyzer 34 may also be configured to transmit and/or receive signals wirelessly via antenna 38. Accordingly, signals useful in the determination of the composition of the extracted gas(es) may be transmitted wirelessly to another computing device which may be associated with a mud logging unit. It should be understood that gas analyzer 34 may also be configured to receive signals wirelessly so that one-way or two-way wireless communication may be conducted with gas analyzer 34 according to known or other methods. Alternatively or in addition, data transfer to and/or from gas analyzer 34 could be conducted using one or more wired connections (not shown).

Figure 2:
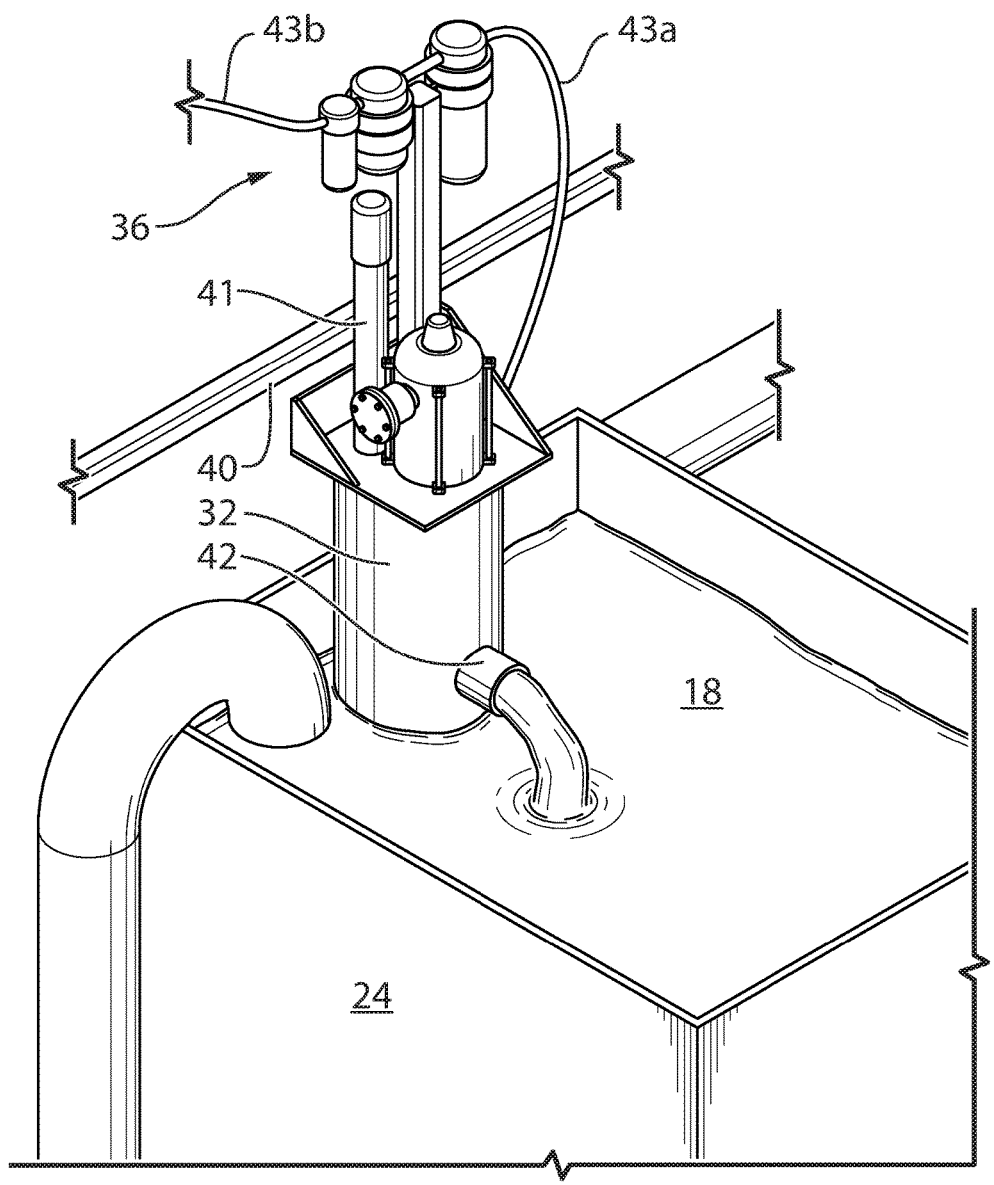
FIG. 2 is a photograph showing an exemplary device for extracting gas(es) from a well-related fluid.

FIG. 2 is a photograph showing an exemplary reservoir 24 containing drilling fluid 18, gas extractor 32 and conditioning unit 36 of installation 10. Reservoir 24 may, for example, be supported on a drilling or other type of rig comprising frame 40. Gas extractor 32 may be supported by reservoir 24 and/or by frame 40. In various embodiments, gas extractor 32 may be directly or indirectly supported by frame 40 and/or other structure(s). The position of gas extractor 32 may be adjustable so that gas extractor 32 may be raised or lowered relative to reservoir 24 depending on the level of drilling fluid 18. For example, gas extractor 32 may be secured to reservoir 24 and/or frame 40 via jack 41, which may be used to adjust the vertical position of gas extractor 32 relative to reservoir 24. The adjustment of the vertical position of gas extractor 32 may be automatic based on a sensed level of drilling fluid 18 or may be done semi-automatically or manually based on a visual inspection of the level of drilling fluid 18 in reservoir 24.

Gas extractor 32 may draw drilling fluid 18 (e.g., drilling mud) in from the bottom of reservoir 24 and exhaust drilling fluid 18 out of outlet 42 above the surface of drilling fluid 18 in reservoir 24. The drawn drilling fluid 18 may be agitated in order to extract gas(es) out of drilling fluid 18. In various embodiments, drilling fluid 18 in reservoir 24 may be circulating (flowing into and/or out of reservoir 24) due to the continuous flow of drilling fluid 18 into and out of well bore 16 during drilling, for example. Gas(es) extracted by gas extractor 32 may be directed to conditioning unit 36 via conduit 43a and gas(es) exiting conditioning unit 36 may be directed to gas analyzer 34 via conduit 43b. In various embodiments, gas analyzer 34 may be in fluid communication directly with gas extractor 32 or indirectly via conditioning unit 36 and/or other intermediate component(s). Conditioning unit 36 may comprise one or more filters to remove some moisture and/or particles from the extracted gas(es). The extracted gas(es) may be drawn and/or propelled continuously or intermittently through conduits 43a, 43b via a pump (see FIG. 5) which may be part of gas analyzer 34 and may induce flow of drilling fluid 18 from gas extractor 32 to gas analyzer 34. In various embodiments the analysis of extracted gas(es) may be conducted continuously or intermittently in substantially real-time (e.g., online) during the drilling or other well-related operation(s).

Gas analyzer 34 may be configured conduct analysis on a moving sample of gas(es). For example, a continuous flow of gas(es) may be flowing through gas analyzer 34 and subsequently exhausted to the atmosphere. Gas analyzer 34 may be configured to conduct spectroscopy on the flow of gas(es) continuously or periodically (i.e., every second or other suitable time interval) and generate data useful in the determination of the composition of the extracted gas(es). The generated data may then be transferred (e.g., wirelessly) to a mud logging unit where the data may be interpreted and/or further analyzed by one or more geologists or mud loggers.

Figure 3:
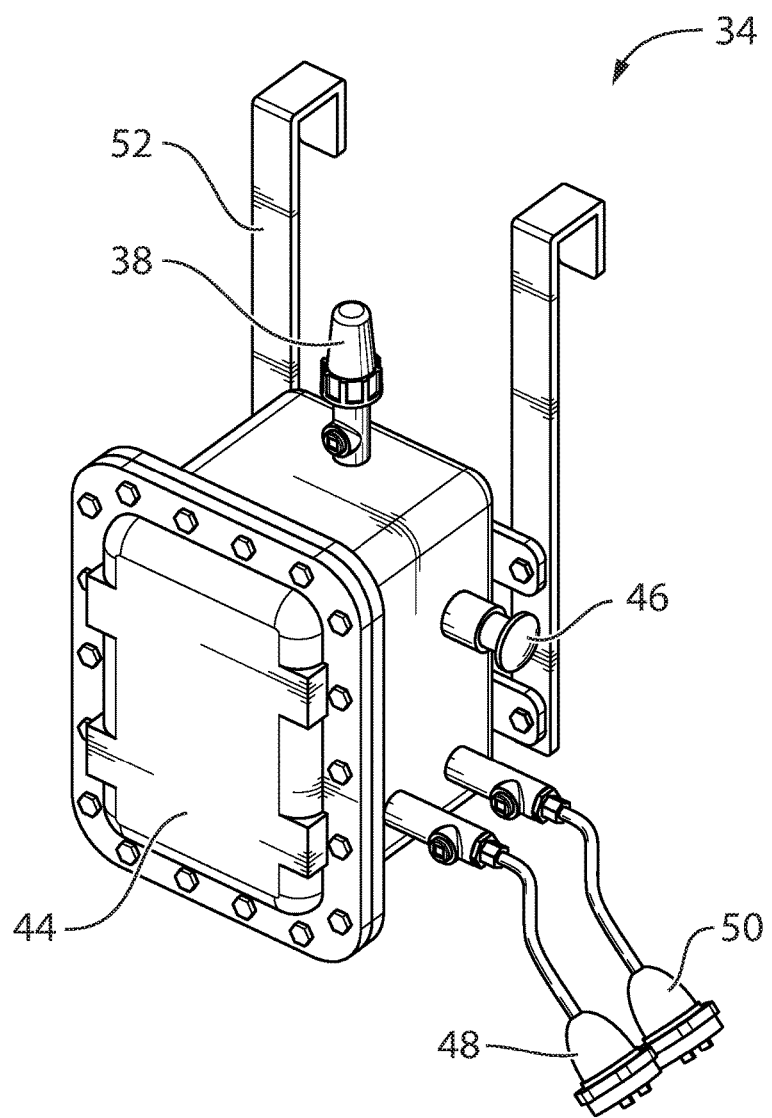
FIG. 3 is a photograph showing an exemplary device for analyzing gas(es)

FIG. 3 is a photograph showing an exemplary embodiment of gas analyzer 34. Gas analyzer 34 may have a relatively rugged and durable construction and accordingly may be configured for use onsite at installation 10 and also for use online and in real-time during the performance of one or more well-related operations at installation 10. For example, gas analyzer 34 may comprise enclosure 44 which may have a metallic (e.g., cast aluminum) construction configured withstand tough environmental conditions associated with well-related operations at installation 10. Enclosure 44 may have a multi-piece construction. For example, enclosure 44 may comprise a container portion and a removable front cover (e.g., lid) securable to the container portion. The front cover may be securable to the container portion via one or more fasteners such as bolts. Also, various components housed inside enclosure 44 may be mounted on shock-absorbing devices (not shown) comprising an elastomeric material such as rubber.

Gas analyzer 34 may comprise on/off switch 46, power inlet 48 and power outlet 50. On/off switch 46 may be a main switch for powering on/off various components of gas analyzer 34. Power inlet 48 may comprise a connector adaptable for connection with a suitable source of power. Power outlet 50 may also comprise a connector for connecting another device to the same power source connected to power inlet 48. Accordingly, power outlet 50 may be used to establish a power connection between gas extractor 32 and the power source to which power inlet 48 of gas analyzer 34 may be connected. Gas analyzer 34 may also comprise one or more gas inlets and one or more gas outlets (shown in FIG. 5) for permitting the flow of extracted gas(es) through gas analyzer 34. Enclosure 44 may be attachable to or comprise one or more suitable brackets 52, which may be used to mount gas analyzer 34 to suitable supporting structure.

Figure 4:
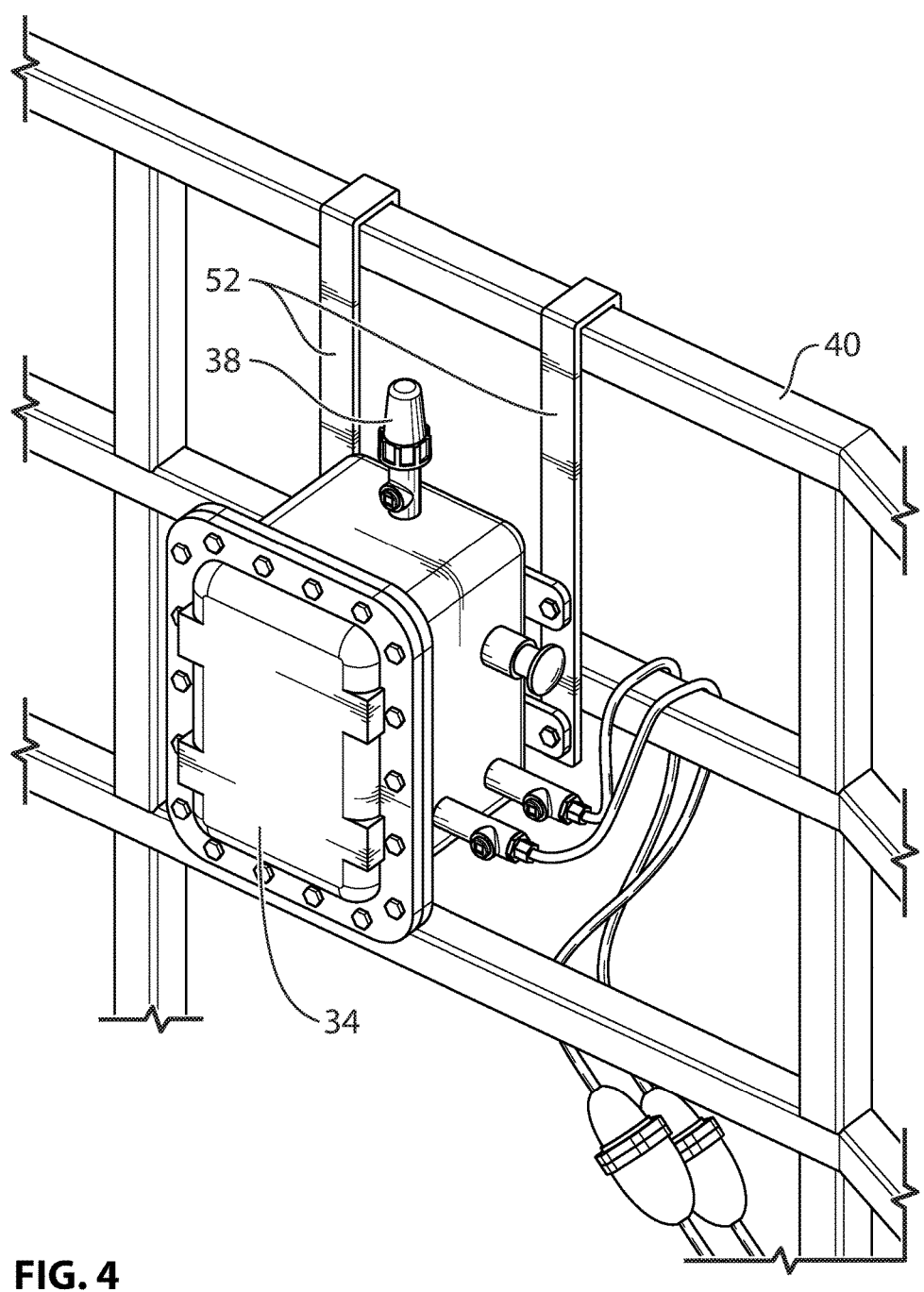
FIG. 4 is a photograph showing the device for analyzing gas(es) of FIG. 3 mounted to a support frame of the installation of FIG. 1.

FIG. 4 is a photograph showing gas analyzer 34 mounted to support frame 40 of installation 10. Gas analyzer 34 may be mounted to any suitable support structure associated with and/or near installation 10. For example, gas analyzer 34 may be mounted to support frame 40, which may be part of installation 10 and which may also be part of a support structure supporting reservoir 24. For example, support frame 40 may comprise a railing that is near reservoir 24. Accordingly, gas analyzer 34 and one or more of reservoir 24, gas extractor 32 and conditioning unit 36 may be directly or indirectly supported by a common support structure.

Figure 5:
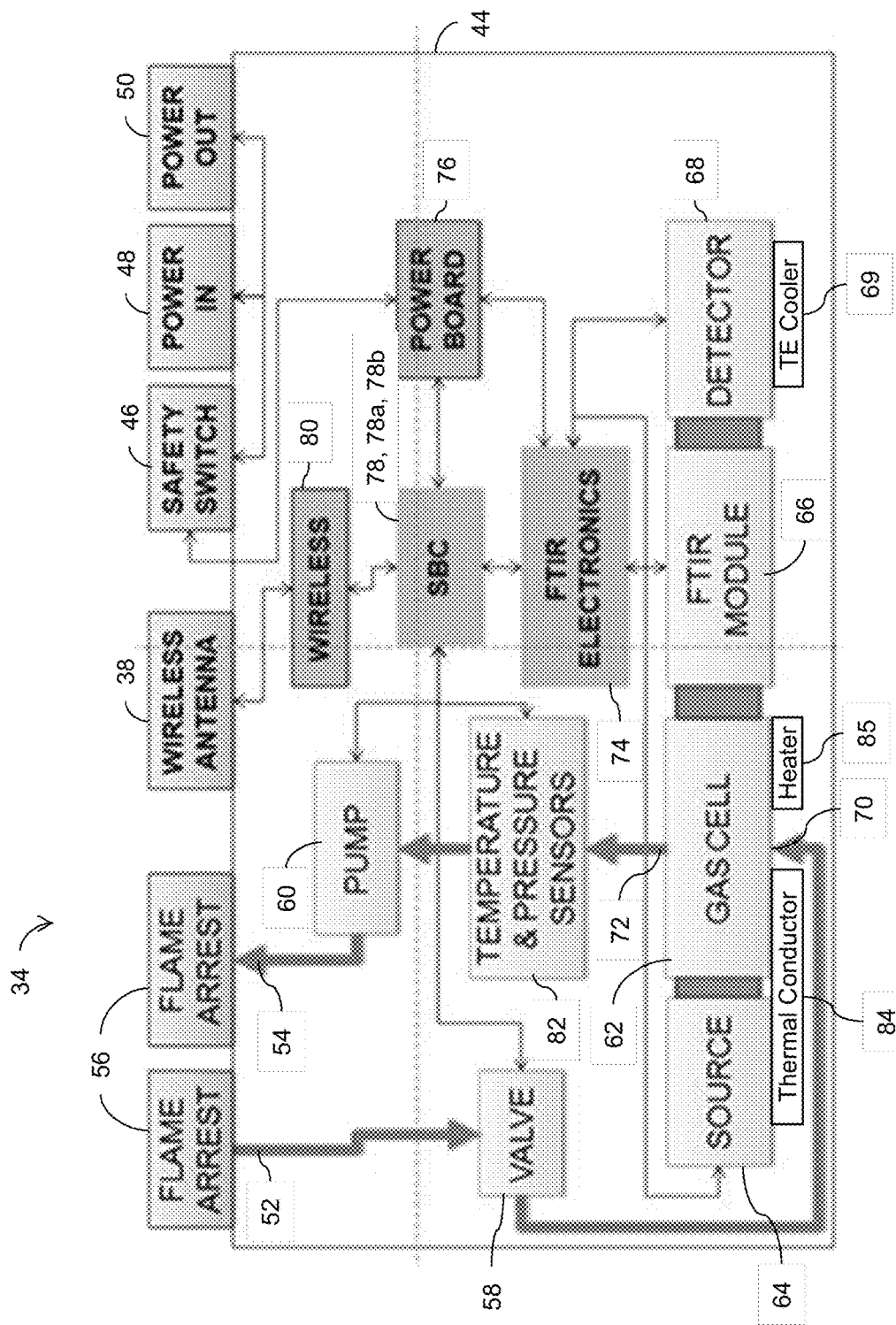
FIG. 5 is a schematic representation of the device for analyzing gas(es) of FIG. 3.

FIG. 5 is a schematic representation of gas analyzer 34 (e.g., instrument, device). As described above, gas analyzer 34 may be configured to conduct FTIR spectroscopy on the gas(es) extracted from drilling fluid 18. Gas analyzer 34 may comprise a number of components housed inside enclosure 44. The relative arrangement of components may be configured to provide a relatively compact envelope for gas analyzer 34. Gas analyzer 34 may comprise one or more gas inlets 52 for permitting gas(es) extracted by gas extractor 32 to enter gas analyzer 34 and one or more gas outlets 54 for releasing the extracted gas(es) after analysis.

As mentioned above, enclosure 44 may comprise one or more features that render enclosure 44 substantially explosion proof. For example, enclosure 44 may comprise one or more flame arrestors 56 associated with gas inlet 52 and gas outlet 54 of gas analyzer 34, that permit the flow of the extracted gas(es) through but will substantially prevent or reduce the risk of sparks exiting enclosure 44 in case of an explosion, spark or fire inside enclosure 44. Antenna 38, switch 46 and any other components associated with enclosure 44 may also be sealed/packaged to be substantially explosion proof. The construction of enclosure 44 and the explosion proofing of enclosure 44 may be in accordance with relevant regulations associated with equipment used near well-related operations. For example, in some embodiments, the construction of enclosure 44 may be in accordance with UL Standard 886 and/or CSA Standard C22.2, both of which being incorporated herein by reference in their entirety, and comprise a Class I or Class II enclosure.

Gas analyzer 34 may comprise one or more flow control devices that may serve to control the flow of gas(es) through gas analyzer 34. For example, such flow control devices may be configured to establish a continuous or intermittent flow of gas(es) through gas analyzer 34. The flow control devices may also be configured to substantially prevent the flow of gas(es) through gas analyzer 34. For example, the flow control devices may comprise one or more valves 58 and/or one or more pumps 60. Valve 58 may be configured to control the flow of gas(es) through inlet 52. For example valve 58 may be configured to adopt fully open, fully closed and/or partially open positions to control the flow of gas(es) through gas analyzer 34. Pump 60 may be disposed within enclosure 44 closer to gas outlet 54 than to gas inlet 52. Accordingly, pump 60 may be configured to induce a flow of gas(es) through gas analyzer 34 by drawing the extracted gas(es) through gas analyzer 34. For example, when gas inlet 52 is in fluid communication with gas extractor 32, pump 60 may be used to draw gas(es) from gas extractor 32 and into gas analyzer 34 via valve 58 when valve 58 is at least partially open.

Gas analyzer 34 may also comprise one or more gas cells 62, one or more radiation sources 64, one or more FTIR modules 66 and one or more detectors 68. Gas cell 62 may comprise one of more cell inlets 70 and one or more cell outlets 72. Cell inlet 70 may be in communication with gas inlet 52 of gas analyzer 34 via valve 58 and cell outlet 72 may be in communication with gas outlet 54 of gas analyzer 34 via pump 60. Gas cell 62 may be configured to hold a quantity of gas(es) during FTIR spectroscopy conducted by gas analyzer 34. For example, gas cell 62 may be configured to permit an intermittent and/or continuous flow of gas(es) through gas cell 62 during FTIR spectroscopy. Gas cell 62 may have a relatively compact construction. For example, gas cell 62 may have an overall length of around 10 cm. In various embodiments, gas cell 62 may have an overall length of less than 15 cm and in some embodiments, may have an overall length of less than 10 cm. For example, gas cell 62 may have a length that is between 5 cm and 15 cm (the length of gas cell is identified in FIG. 7).

The length of gas cell 62 may be selected based on the type(s) of hydrocarbon(s) to be detected from extracted gas(es). For example, a shorter length (i.e., 1 cm) may be preferred for detecting methane (C1) and a longer length (e.g., 15 cm) may be preferred for detecting pentane (C5). The length of gas cell 62 may be selected based on the spectroscopic property(ies) of the one or more constituents to be detected. In various embodiments, the length of gas cell 62 may be selected to provide substantially optimum detectability of one or more constituents of extracted gas(es) or, alternatively, the length of gas cell 62 may be selected to permit a number of constituents of extracted gas(es). For example, a length of around 10 cm may be suitable for detecting hydrocarbons such as methane (C1), ethane (C2), propane (C3), butane (C4) and pentane (C5).

As explainer further below, the structure of gas cell 62 may be configured to permit the passage of at least some radiated energy (i.e., electromagnetic radiation) therethrough to permit the interaction between the radiation and the gas(es) contained in gas cell 62. Accordingly, source of radiation 64 may be configured to direct radiated energy into gas cell 62 and detector 68 may be configured to detect radiated energy coming out of (i.e., having passed through) gas cell 62. Thermoelectric cooler 69 may be associated with detector 68 for cooling of detector 68 during operation. Source of radiation 64 may comprise a relatively broadband light source that emits radiation in the full spectrum of wavelengths of interest depending on the specific application and on the type of constituents expected to be detected in extracted gas(es). For example, for the detection of hydrocarbons such as methane, ethane, propane, butane and pentane, wavelengths of interest may include those in the mid infrared range (e.g., between 5 μm and 13.5 μm) and source of radiation 64 may be configured to output radiation in at least that same range of wavelengths and optionally also outside of the mid infrared range. In various embodiments, source 64 may comprise one or more polychromatic infrared sources, (e.g., black-body radiator) and/or other tunable or other types of sources of radiation suitable for FTIR spectroscopy in the desired range of wavelengths. For example, source 64 may comprise an incandescent element that emits broadband infrared radiation. In any case, source of radiation 64 may be configured to direct a substantially collimated beam of radiation toward and through gas cell 62.

FTIR module 66 may be configured to interact with radiation emitted by radiation source 64. For example, FTIR module 66 may be disposed in the optical path of the radiation emitted by source 64 between gas cell 62 and detector 68. FTIR module 66 may, for example, comprise one or more interferometers such as a Michelson interferometer adapted for FTIR spectrometry. The structure and operation of Michelson interferometers is known and will not be described further herein. In various embodiments, FTIR module 66 and detector 68 may be used to obtain one or more interferograms (e.g., raw data representing light/radiation intensity/absorption for each position of the movable mirror in the Michelson interferometer) for the radiation that has passed through gas cell 62. At least some aspect of the operation of FTIR module 66 may be controlled via suitable FTIR electronics 74. Detector 68 may comprise one or more photosensors or photodetectors (i.e., sensors of light or other electromagnetic energy). Detector 68 may be of known or other types and may be configured to produce one or more signals representative of the intensity(ies) of radiation received at detector 68 from source 64.

Gas analyzer 34 may also comprise one or more power supplies such as power boards 76 and one or more processing devices such as single board computer (SBC) 78. Power board 76 may be configured to receive electrical power from power inlet 48 via switch 46 and conduct appropriate power conditioning (e.g., rectification, voltage step up/down, etc.) suitable for powering SCB 78 and optionally other components of gas analyzer 34 including one or more of pump 60, valve 58, source 64, FTIR module 66, detector 68, FTIR electronics 74, modem 80 and one or more sensors 82. In various embodiments, some or all components inside enclosure 44 requiring electrical power may be powered via power board 76. In various embodiments, FTIR electronics 74 may handle lower level functions of FTIR module 76 (e.g., interferometer) and/or other functions. For example, FTIR electronics 74 may handle functions such as controlling radiation source 64, acquiring intensities via detector 68, movement of the movable mirror in FTIR module 66 and the acquisition of one or more interferograms.

Gas analyzer 34 may also comprise one or more thermal conductors 84 thermally coupled to both source 64 and gas cell 62. Thermal conductor 84 may comprise part of enclosure 44 or comprise one or more separate component made at least in part from a thermally conductive material. Thermal conductor 84 may serve to conduct heat from source 64 to gas cell 62 during operation. In various embodiments, source 64 may be disposed in relatively close proximity to gas cell 62 so that a length of thermal conductor 84 may be kept relatively short so that heat from source 64 to gas cell 62 may be conducted over a relatively short distance. The distance between source 64 and gas cell 62 may be selected based on the intensity of the radiation (i.e., power) output by source 64, the amount of waste heat generated by source 64 during use and also the amount of heat transfer desired from source 64 to gas cell 62. For example, the distance between source 64 and gas cell 62 may be about 5 mm for a 15-watt source 64. In various embodiments, the distance between source 64 and gas cell 62 may be between about 3 mm and about 20 mm. The distance may be selected to be sufficient to substantially prevent damage of optical components of gas cell 62 by radiation while at the same time also providing a suitable amount of heat transfer from source 64 to gas cell 62.

Source 64 may also transfer heat to gas cell 62 via the radiation that is output from source 64 and directed into gas cell 62. Accordingly, the above values of distances between source 64 and gas cell 62 may, in some embodiments, also be suitable to permit a desired amount of heating of gas cell 62 by radiation from source 64.

Gas analyzer 34 may also comprise auxiliary heater 85, which may be used to actively heat at least a portion of gas cell 62 by conduction and/or convection. The operation of auxiliary heater 85 may be controlled by SBC 78 and/or FTIR electronics 74. Auxiliary heater 85 may be powered via power board 76.

Figure 6:
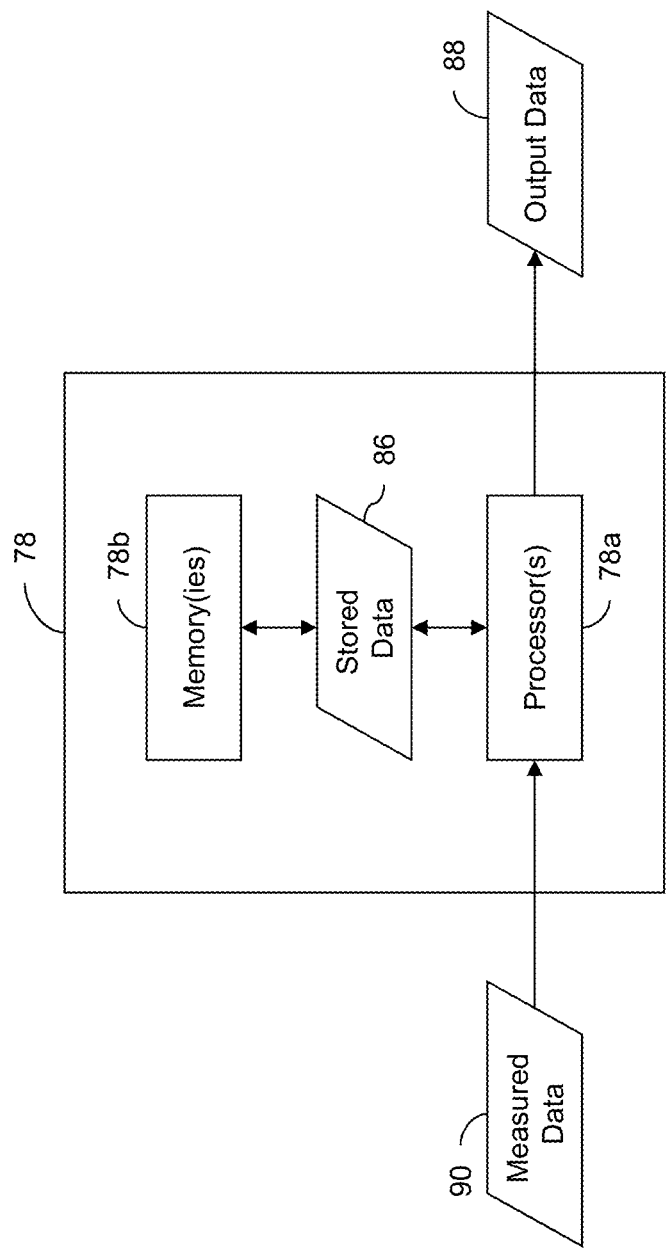
FIG. 6 shows a partial schematic representation of a data processing device of the device for analyzing gas(es) of FIG. 3.

FIG. 6 shows a partial schematic representation of a data processing device (e.g., SBC 78) of gas analyzer 34. SBC 78 may comprise one or more data processors 78a and related accessories that enable control of at least some aspects of performance of gas analyzer 34. SBC 78 may for example be configured to make decisions regarding the control and operation of gas analyzer 34 and cause one or more actions to be carried out based on machine-readable instructions including those stored onboard SBC 78 and/or other machine-readable instructions received via modem 80. As data processors, SBC 78 may include one or more microcontrollers or other suitably programmed or programmable logic circuits. SBC 78 may also comprise memory(ies) and memory data devices or register(s) (referred hereinafter as "memory 78b"). Memory 78b may comprise any storage means (e.g., devices) suitable for retrievably storing machine-readable instructions executable by data processor 78a of SBC 78 and other data. Memory 78b may be non-volatile and may include erasable programmable read only memory (EPROM), flash memory, and/or other electromagnetic media suitable for storing electronic data signals in volatile or non-volatile, non-transient form. Memory may contain machine-readable instructions for execution by processor 78a of SBC 78 and also stored data 86. Such machine-readable instructions may cause SBC 78 to carry out various methods disclosed herein including the generation of signals (e.g., output data 88) useful in the determination of the composition of the extracted gas(es) in gas cell 62. Stored data 86 may also comprise expected spectral data (e.g., stored intensities and/or absorbance values) such as that shown in FIGS. 10A-10H, associated with hydrocarbons or other expected constituents of the extracted gases for use by SBC 78 in the generation of one or more signals useful in the determination of the composition of the extracted gas(es).

SBC 78 may be configured (e.g., via machine-readable instructions) to control and/or coordinate one or more aspects of the operation of gas analyzer 34. For example, SBC 78 may be configured to control and coordinate one or more components, monitoring one or more pressures, monitoring one or more temperatures, acquisition of measured data 90 (e.g., intensity/absorption values, interferograms), providing power (e.g., from power board 76) to various components and conducting some data processing using measured data 90. SBC 78 may also be configured to, according to machine-readable instructions, transform the measured data 90 (e.g., raw data including intensity/absorption for each mirror position) into more desirable results (i.e., light intensity/absorption for each wavelength). In other words, the processing conducted by SBC 78 may include conducting Fourier transform of the raw data.

SBC 78 may also be configured to determine, using measured data 90, concentrations of one or more constituents (e.g., hydrocarbons) of interest according to machine-readable instructions and stored data 86. In various embodiments, the operation of SBC 78, including the determination of the concentration(s) of one or more constituents may be controlled based on commands and/or data received via modem 80.

Figure 7:
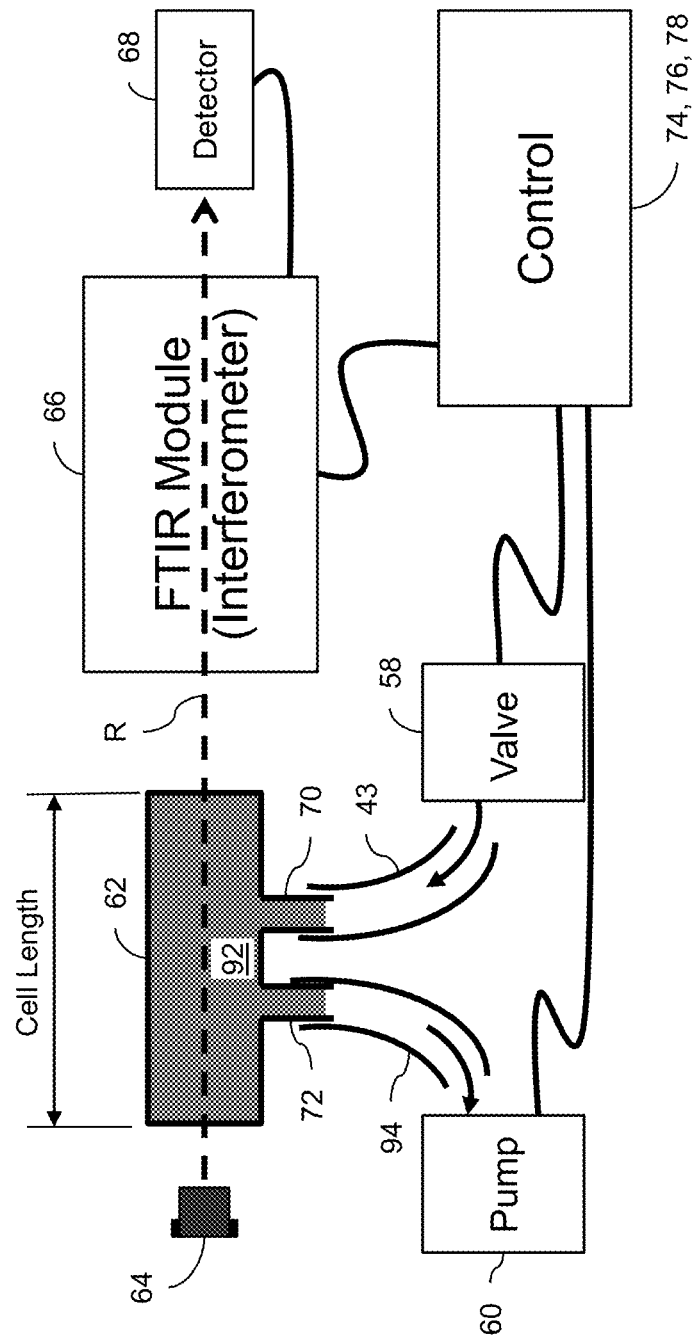
FIG. 7 is a schematic representation of a portion of the device for analyzing gas(es) of FIG. 3.

FIG. 7 is a schematic representation of a portion of gas analyzer 34. Gas cell 62 may comprise one or more cavities 92 through which radiation R may be transmitted. Cavity 92 may be configured to receive gas(es) via cell inlet 70 and release gas(es) via cell outlet 72. Cavity 92 may define a gas passage between cell inlet 70 and cell outlet 72. The gas passage defined by cavity 92 may be configured (e.g., have an appropriate length, size, shape, etc.) to permit a substantially laminar flow of extracted gas(es) to occur inside at least a portion of cavity 92 at a desired or expected flow rate. Cell inlet 70 may be in fluid communication with gas extractor 32 via inlet conduit 43 and valve 58. Cell outlet 72 may be in fluid communication with the atmosphere via outlet conduit 94 and pump 60. In various embodiments, valve 58 may be disposed upstream of gas cell 62 and pump 60 may be disposed downstream of gas cell 32. Accordingly, the operation of pump 60 may cause a flow of extracted gas(es) to be drawn (via suction) into cavity 92 from gas extractor 32 via cell inlet 70, conduit 43 and valve 58. Some aspects of operation of pump 60, valve 58, FTIR module 66 and/or detector 68 may be controlled by suitable control circuitry including one or more of FTIR electronics 74, SBC 78 and power board 76.

Figure 8:
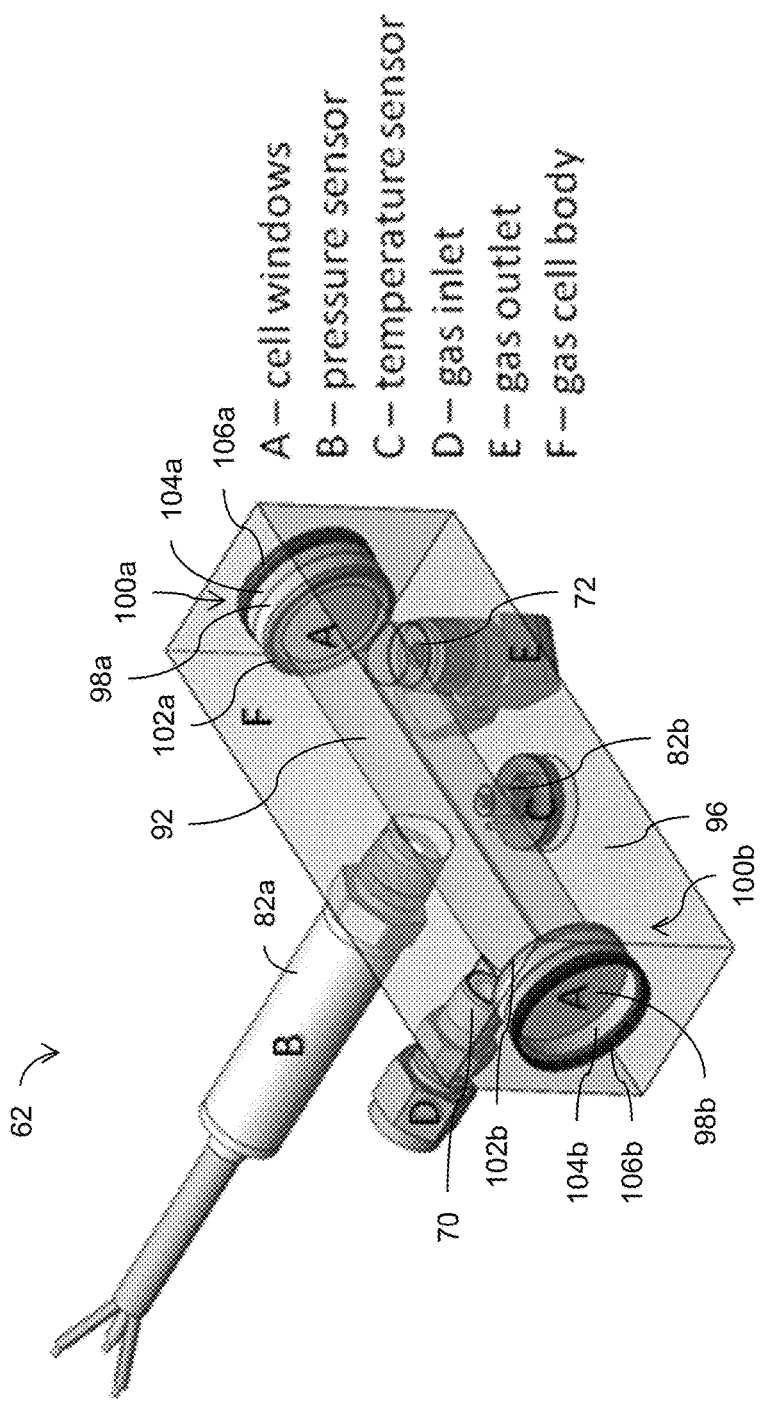
FIG. 8 is an axonometric view of a gas cell of the device for analyzing gas(es) of FIG. 3.

FIG. 8 is an axonometric view of an exemplary gas cell 62, which may be suitable for use with gas analyzer 34. Gas cell 62 may comprise one or more bodies 96, into which cavity(ies) 92 may be defined. Body 96 is shown as being partially transparent in FIG. 7 for the purpose of illustration of other components of gas cell 62 but it should be understood that body 96 does not have to be partially transparent. In various embodiments, body 96 may comprise a metallic material and/or other thermally conductive material which may facilitate the conduction of heat from source 64 via thermal conductor 84 (shown in FIG. 5). In various embodiments, cavity 92 may have a generally cylindrical shape having a substantially circular cross-section. Sensors 82a, 82b may be removably secured to body 96.

At each end of cavity 92, one or more windows 98a, 98b may be removably installed. Windows 98a, 98b may be at least partially transparent to the radiation R produced by radiation source 64 so that at least some of the radiation within the range of wavelengths of interest may be transmitted through gas cell 62 and be detected by detector 68. One or more of windows 98a, 98b may be removably installed with body 96 to permit removal of windows 98a, 98b and permit servicing of gas cell 62. In various embodiments, body 96 may comprise one or more interfaces 100a, 100b to permit the removable installation of windows 98a, 98b with body 92. For example, interfaces 100a, 100b may be configured to removably retain windows 98a, 98b during operation of gas cell 62. For example, interfaces 100a, 100b may provide any suitable type of fastening mechanism(s) permitting removal (and optionally the re-installation) of windows 98a, 98b for servicing of gas cell 62. In various embodiments, the servicing of gas cell 62 may include the removal, cleaning and reinstallation of one or more of windows 98a, 98b. Alternatively, the servicing of gas cell 62 may include the removal of one or more of windows 98a, 98b and the installation of one or more replacement windows. The servicing of gas cell 62 may also include the cleaning of cavity 92 when one or more of windows 98a, 98b have been removed.

Interfaces 100a, 100b may also permit a substantially hermetic seal to be formed between windows 98a, 98b and body 96. In various embodiments, the hermetic seal may be configured to withstand at least some differential pressure between cavity 92 and the atmosphere. It should be understood that the hermetic seal may not be absolutely hermetic but may provide some sealing suitable for the purpose of conducting FTIR spectrometry using gas analyzer 34 as described herein. As mentioned above, it is expected that gas(es) extracted by gas extractor 32 may contain atmospheric air so, in various embodiments, it may not be necessary that absolute hermetic sealing be provided. For example, one or more suitable sealing members 102a, 102b may be provided to establish at least some sealing between windows 98a, 98b and body 96. In various embodiments, sealing members 102a, 102b may comprise compressible seals disposed between windows 98a, 98b and body 96 at respective interfaces 100a, 100b. For example, sealing members 102a, 102b, may comprise suitable gaskets, o-rings and/or other suitable type(s) of seals. In various embodiments, sealing members 102a, 102b may be releasable and optionally also reusable.

In various embodiments windows 98a, 98b may be removably installed with body 96 via respective threaded retaining rings 104a, 104b and respective annular spacers 106a, 106b. For example, with respect to the installation of window 98a, sealing member 102a may first be installed into interface 100a and then window 98a may be inserted into interface 100a so that sealing member 102a may form a seal between body 96 and window 98a. Next, spacer 106a may be inserted into interface 100a behind window 98a and retainer ring 104a may be inserted behind spacer 106a by engagement with corresponding threads formed into body 96. The threading in of retainer ring 104a may push onto spacer 106a, which may in turn push against window 98a and thereby cause some compression of sealing member 102a between body 96 and window 98a. Body 96 may also comprise a suitable seating surface against which sealing member 102a may be seated during installation. It should be understood that the installation of window 98b may be substantially similar to the installation of window 98a. Alternatively, the installation of window 98b may be different from the installation of window 98a.

During operation, gas analyzer 34 may be used to conduct online analysis of gas(es) extracted by gas extractor 32 from drilling fluid 18 or other well-related fluid(s) during well-related operations. In various embodiments, gas analyzer 34 may be suitable for use online and in real-time while a well-related operation such as drilling is being conducted and also at or near the site where such well-related application is being performed. For example, gas analyzer 34 may be configured to be in fluid communication with a source of drilling fluid 18 so that the analysis of gas(es) extracted from drilling fluid 18 may be conducted substantially in real-time while the well-related operation is being carried out so that the results of the analysis obtained via gas analyzer 34 may be used to make decisions about the ongoing well-related operation and permit operators of drilling rigs, for example, to take the appropriate actions.

Figure 9:
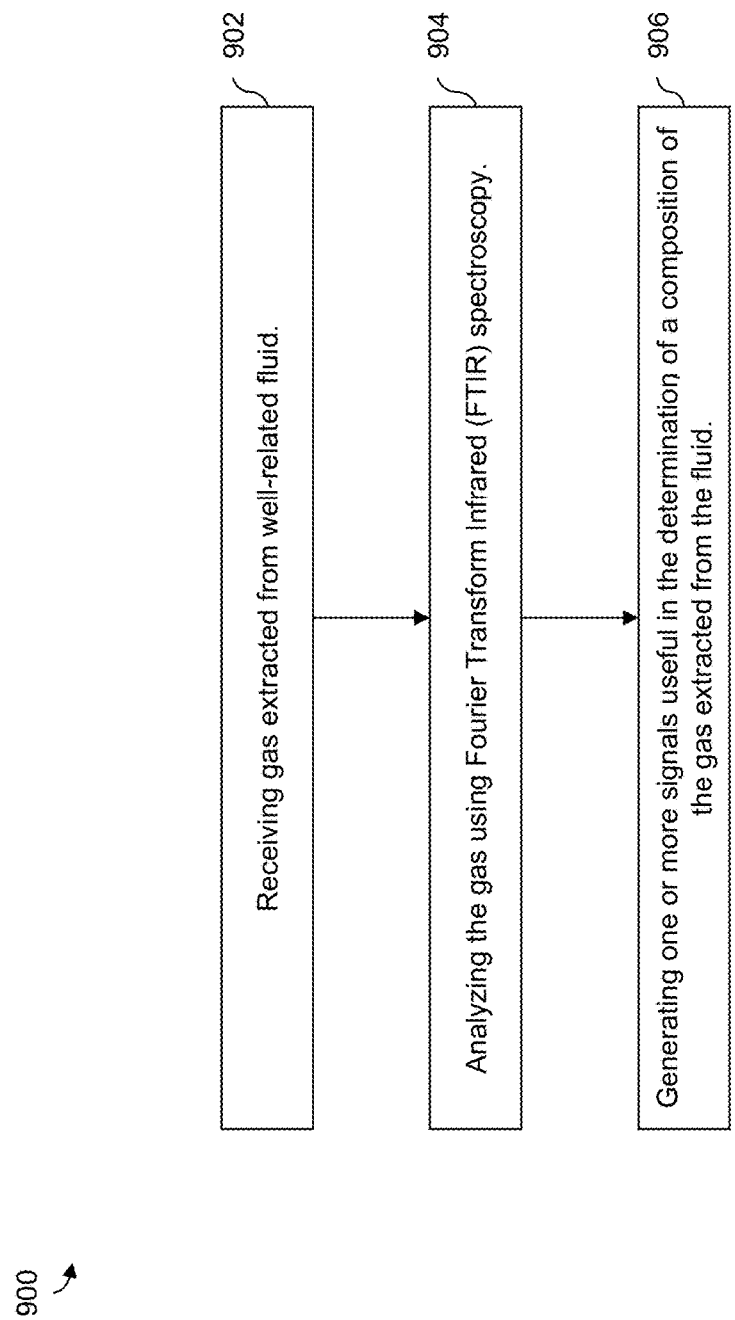
FIG. 9 is a flowchart illustrating an exemplary method for analyzing gas(es) extracted from well-related fluid.

FIG. 9 is a flowchart illustrating an exemplary method 900 for real-time analysis of gas(es) extracted from a fluid associated with an ongoing well-related operation. Method 900 may be conducted substantially in real-time while the well-related application is being carried out. Method 900 may comprise: receiving gas(es) extracted from fluid such as drilling fluid 18 associated with the well-related operation (see block 902); analyzing the gas(es) using Fourier Transform Infrared (FTIR) spectroscopy (see block 904); and generating one or more signals useful in the determination of a composition of the gas(es) extracted from the fluid (see block 906).

Method 900 may be carried out using gas analyzer 34 under the guidance and/or control of SBC 78 and/or FTIR electronics 74 and based on machine-readable instructions executable by processor within SBC 78 and/or FTIR electronics 74. As mentioned above, the FTIR spectroscopy may be conducted using wavelengths in the mid infrared range or other suitable range of wavelengths depending on the constituents of the extracted gas(es) that is/are of interest. For example, wavelengths between 5 µm and 13.5 µm may be used so that methane, ethane, propane, butane, pentane (i.e., hydrocarbons C1 to C5) exhibit distinguishable absorbance peaks within that range. In various embodiments, the range of wavelengths may be selected so that methane, ethane, propane, butane, pentane, hexane, heptane and octane (i.e., hydrocarbons C1 to C8) exhibit distinguishable absorbance peaks and may be distinguished. For example, wavelengths between 5 µm and 13.5 µm may also be suitable for detecting one or more of methane, ethane, propane, butane, pentane, hexane, heptane and octane (i.e., hydrocarbons C1 to C8).

Figure 10A:
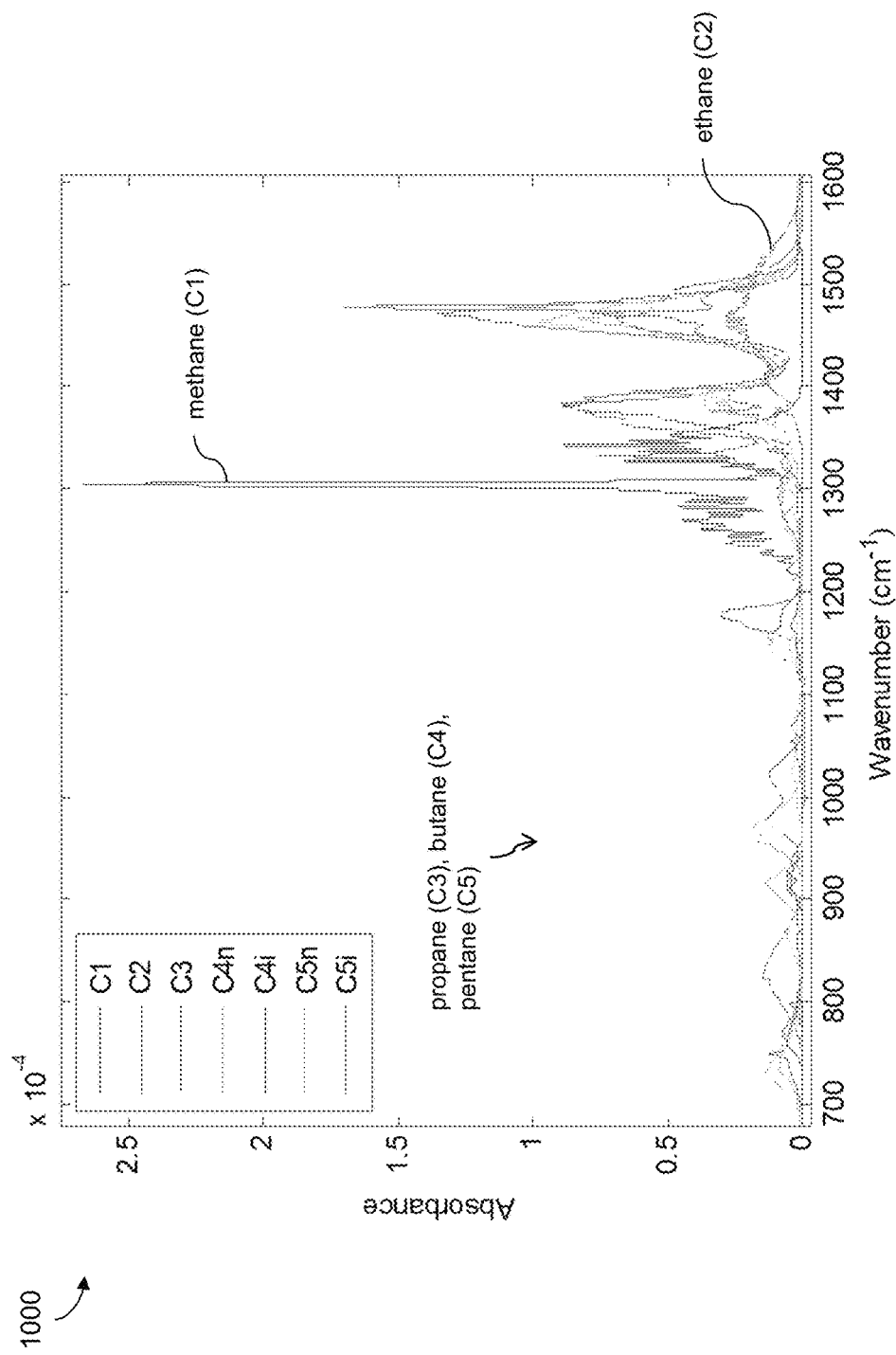
FIG. 10A is a plot showing absorbance data for hydrocarbons versus wavenumber.
Figure 10B:
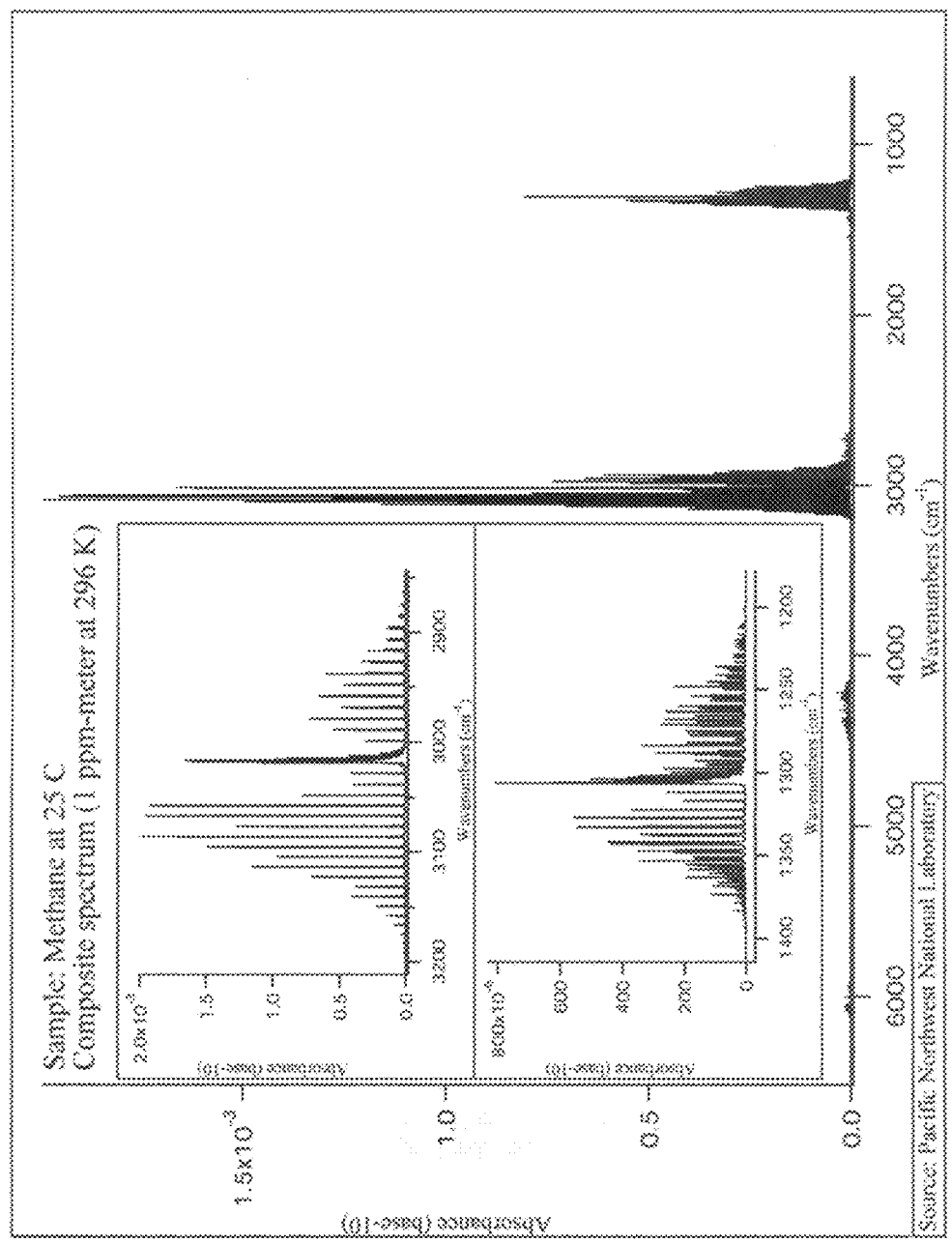
FIG. 10B illustrates plots of absorbance data for methane at 25° C. versus wavenumber.
Figure 10C:
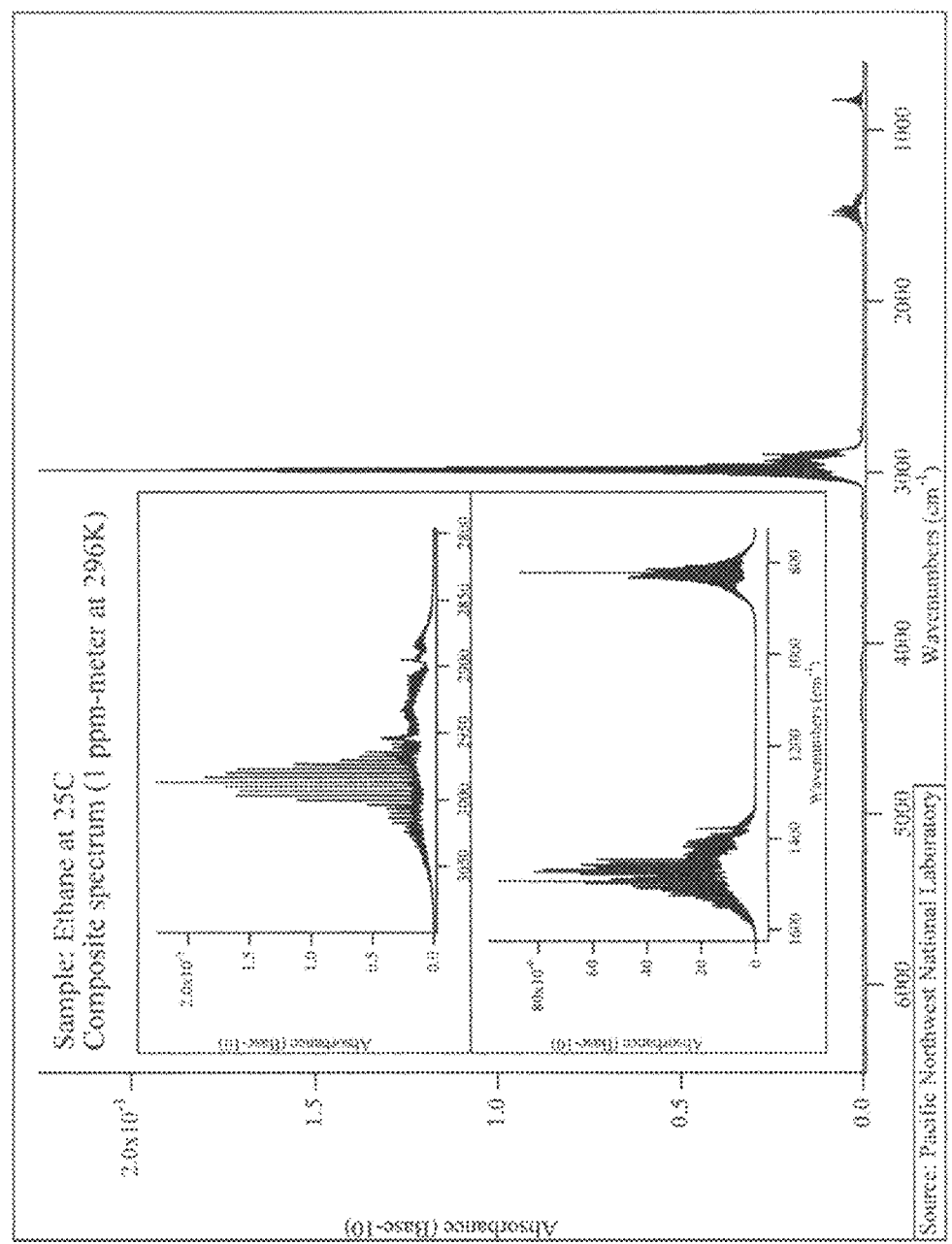
FIG. 10C illustrates plots of absorbance data for ethane at 25° C. versus wavenumber.
Figure 10D:
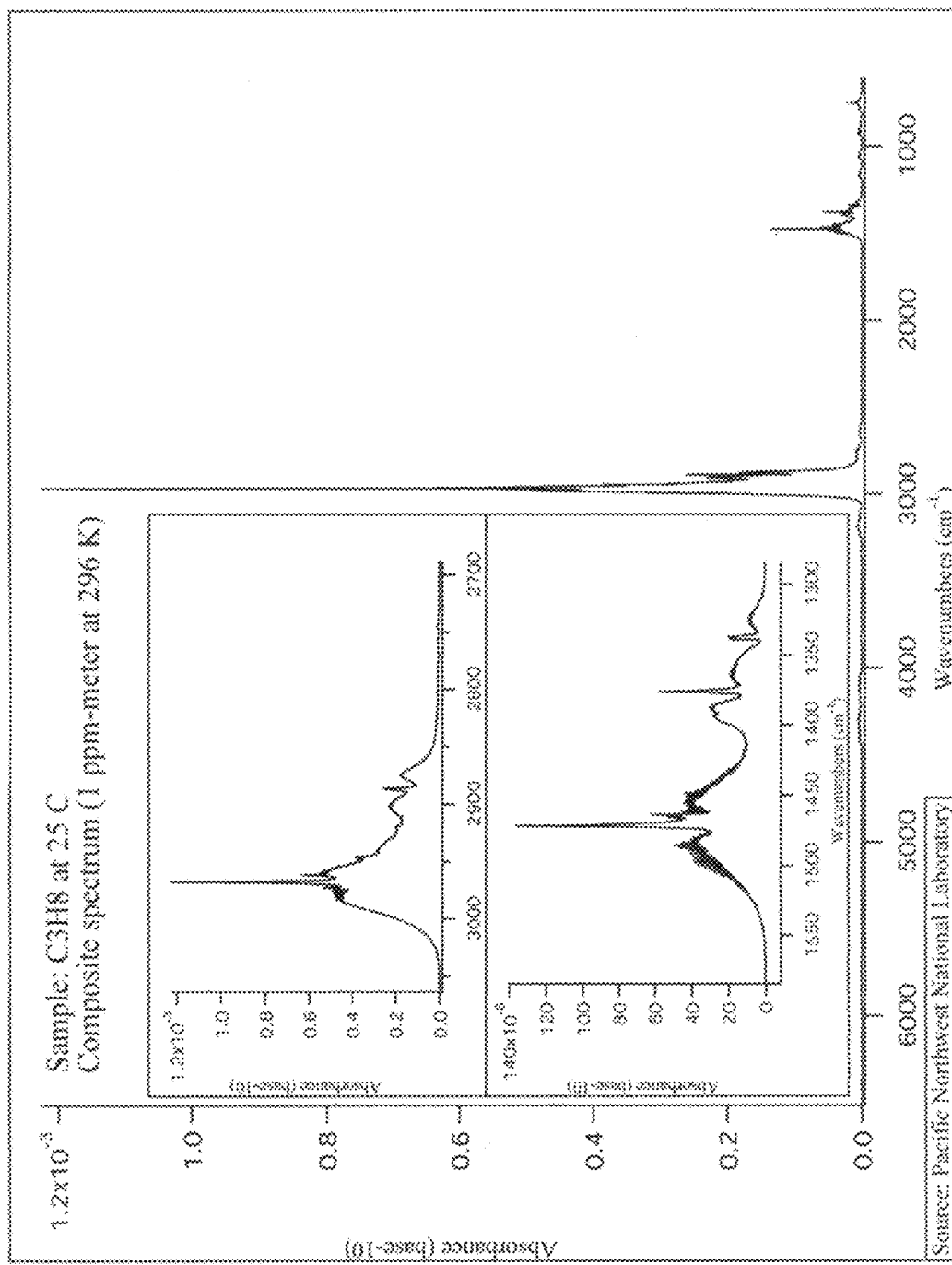
FIG. 10D illustrates plots of absorbance data for propane ($C_3H_8$) at 25° C. versus wavenumber.
Figure 10E:
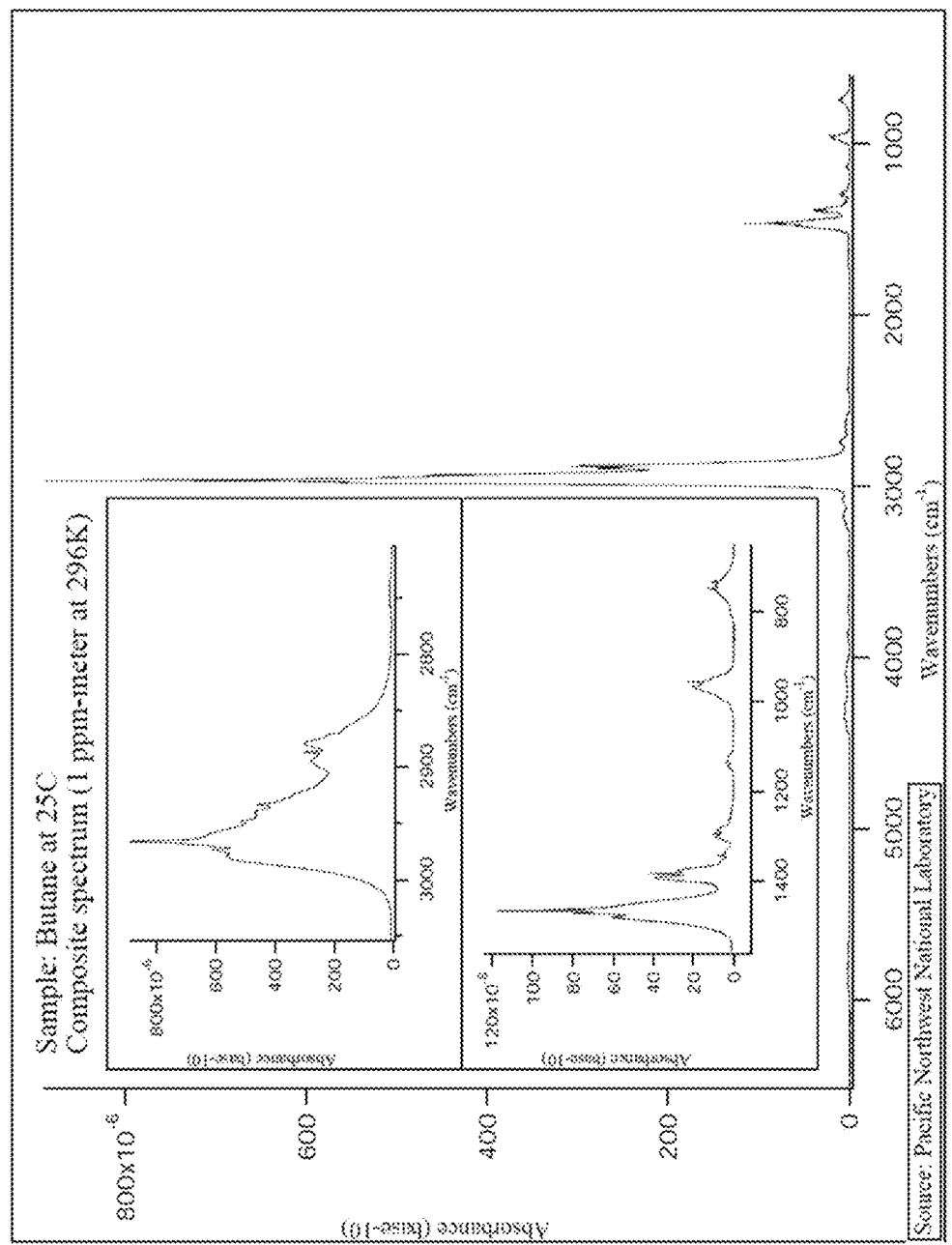
FIG. 10E illustrates plots of absorbance data for butane at 25° C. versus wavenumber.
Figure 10F:
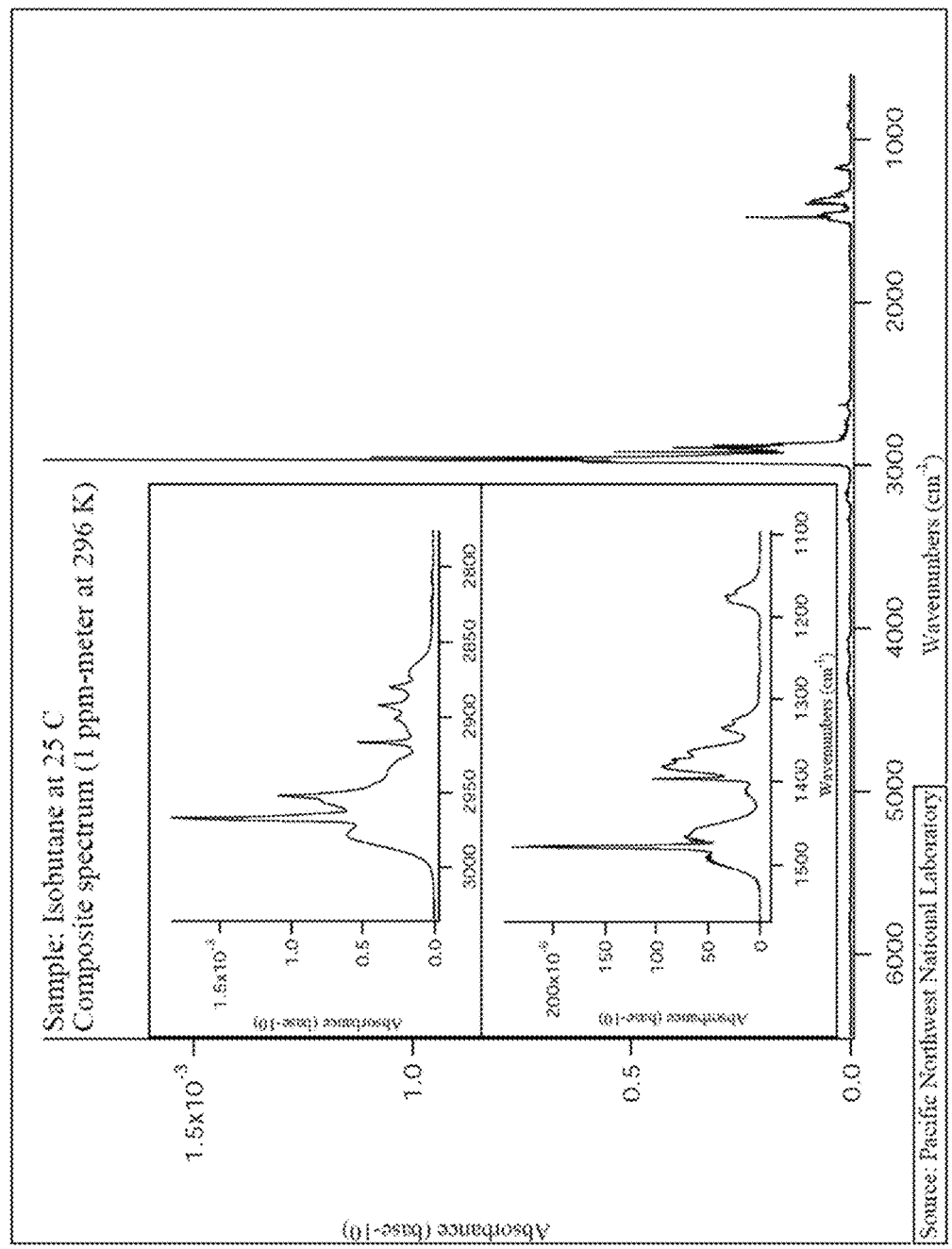
FIG. 10F illustrates plots of absorbance data for isobutane at 25° C. versus wavenumber.
Figure 10G:
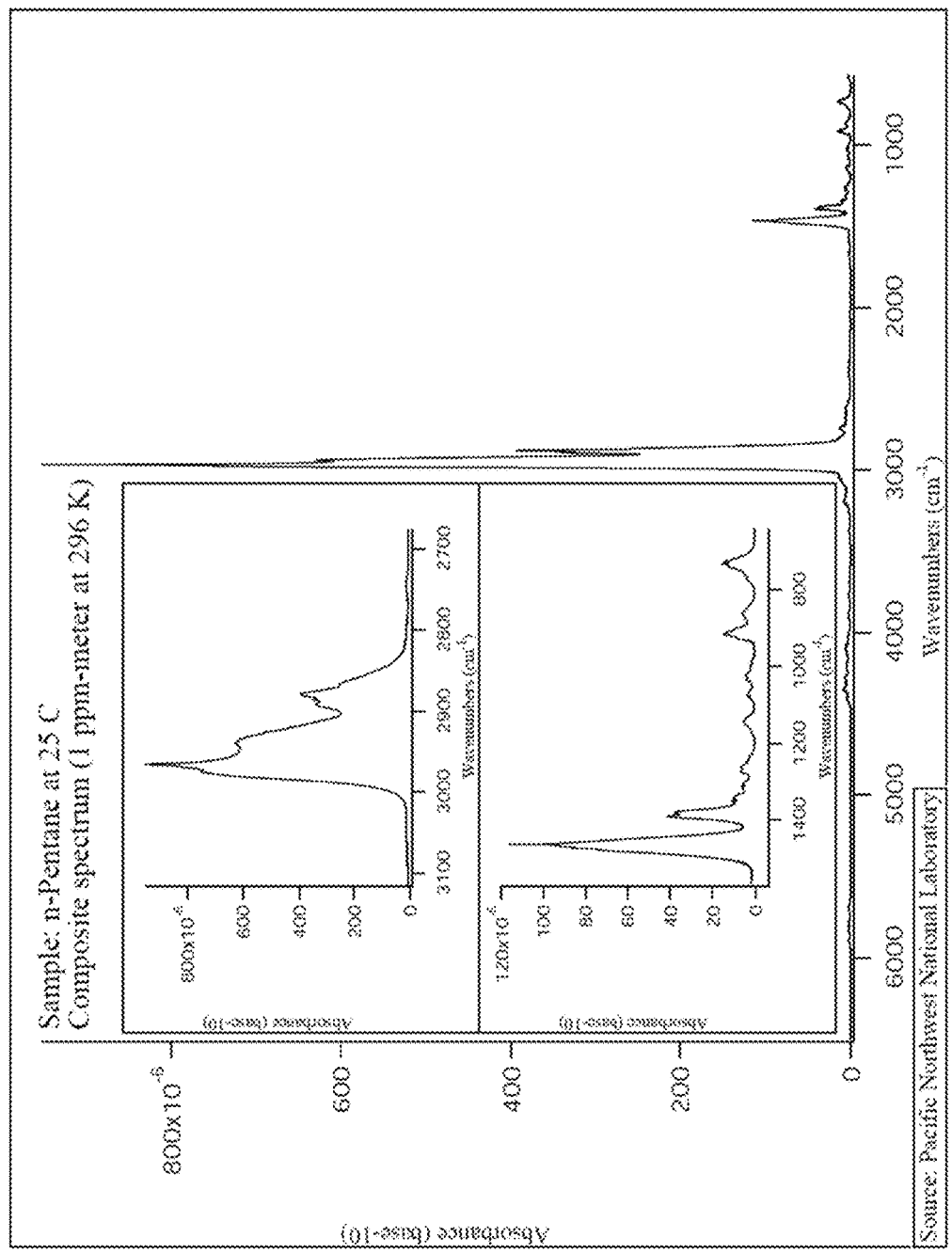
FIG. 10G illustrates plots of absorbance data for n-pentane at 25° C. versus wavenumber.
Figure 10H:
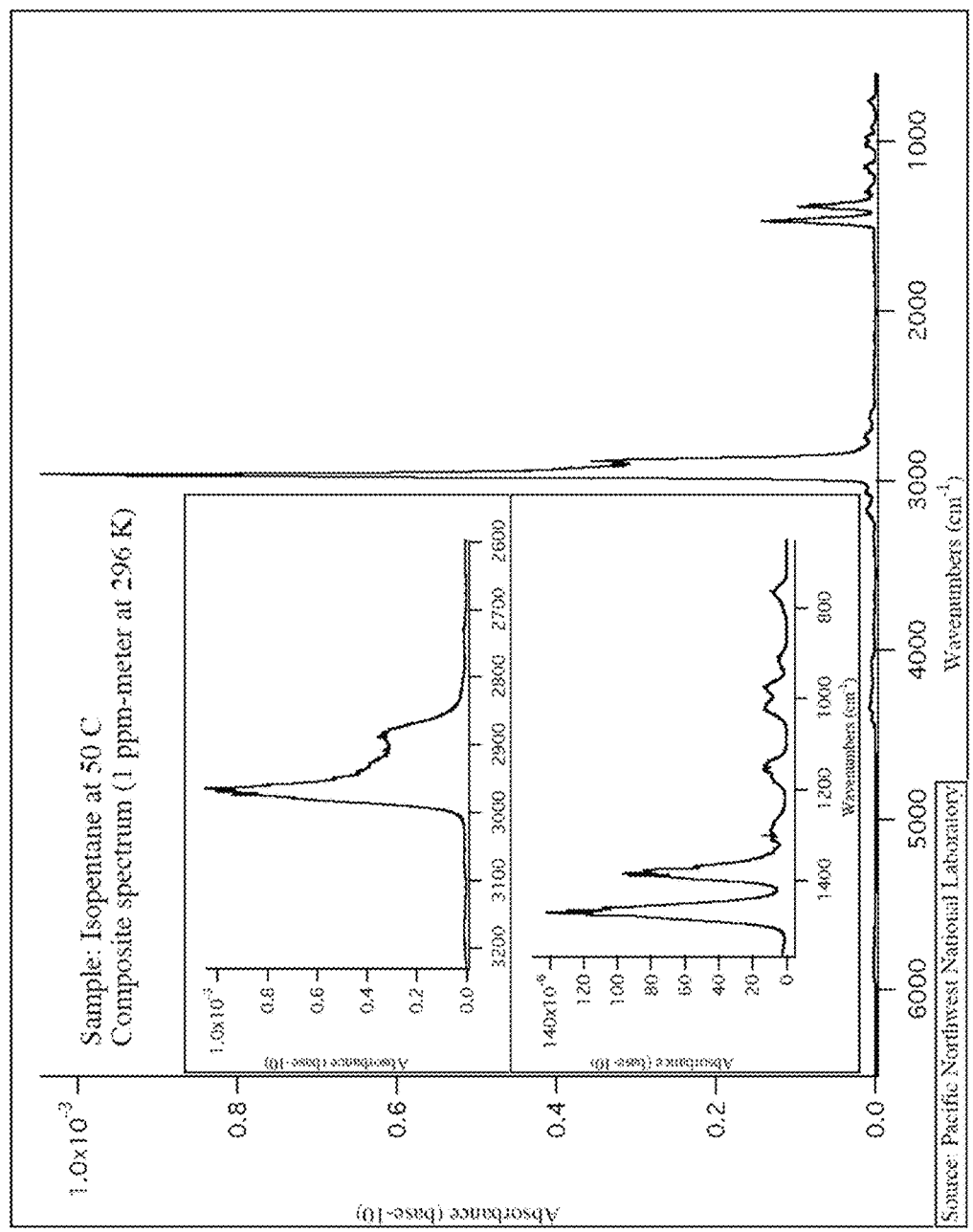
FIG. 10H illustrates plots of absorbance data for isopentane at 50° C. versus wavenumber.

FIG. 10A shows plot 1000 of absorbance values of hydrocarbons (C1 to C5) versus wavenumber expressed in $cm^{-1}$. FIGS. 10B-10H show plots of absorbance data versus wavenumber for the following hydrocarbons respectively: methane, ethane, propane, butane, isobutane, n-pentane and isopentane. FIGS. 10A-10H show absorbance data for pure hydrocarbon gases published by the Pacific Northwest National Laboratory (PNNL). In reference to FIG. 10A, plot 1000 shows that hydrocarbons C1-C5 exhibit distinguishable absorbance peaks in the range of wavenumbers between 700 $cm^{-1}$ to 1600 $cm^{-1}$ corresponding to a range of wavelengths between about 6.25 µm to about 14.3 µm under certain conditions. Absorbance data such as that shown in FIGS. 10A-10H or portion(s) thereof may be stored in memory 78b as stored data 86 (see FIG. 6) or be otherwise available to processor 78a of SBC 78 for the purpose of generating signals (e.g., output data 88 shown in FIG. 6) useful in the determination of the composition of the gas(es) extracted from drilling fluid 18.

In various embodiments, the generation of output data 88 may be based on a comparison of measured data 90 (e.g., interferogram) with stored data 86 according to machine-readable instructions executable by processor 78a. For example, output data 88 may be useful in the identification of one or more hydrocarbons such as methane, ethane, propane, butane, pentane, hexane, heptane and octane in the extracted gas(es). For example, output data 88 may be indicative of a concentration of one or more of such hydrocarbons in the extracted gas(es). Alternatively, in various embodiments, output data 88 may be representative of measured data 90 and the comparison of measured data 90 with stored data 86 may be conducted elsewhere such as by a computing device other than SBC 78. Accordingly, output data 88 may be transmitted to the other computing device(s) via modem 80. In any event, whether or not the comparison is done by SBC 78, output data 88 may nonetheless be useful in the determination of the composition of the gas(es) extracted from drilling fluid 18. In various embodiments, output data 88 may be representative of concentration(s) of one or more hydrocarbons in the extracted gas(es).

Referring again to method 900, output data 88 generated by SBC 78 may be stored in memory 78b and/or transmitted via modem 80 to another location or computing device(s). For example, output data 88 may be transmitted in the form of wireless signals directly or indirectly (e.g., via WiFi or cellular communication) to one or more other computing devices associate with mud logging activities related to one or more well-related operations.

The analysis conducted by gas analyzer 34 may also be conducted on a continuous flow of gas(es) extracted from the fluid. Due to the configuration of gas cell 62, the continuous flow of extracted gas(es) through cavity 92 may be substantially laminar through at least a portion of cavity 92 and at least for some expected flow rates of extracted gas(es).

Figure 11:
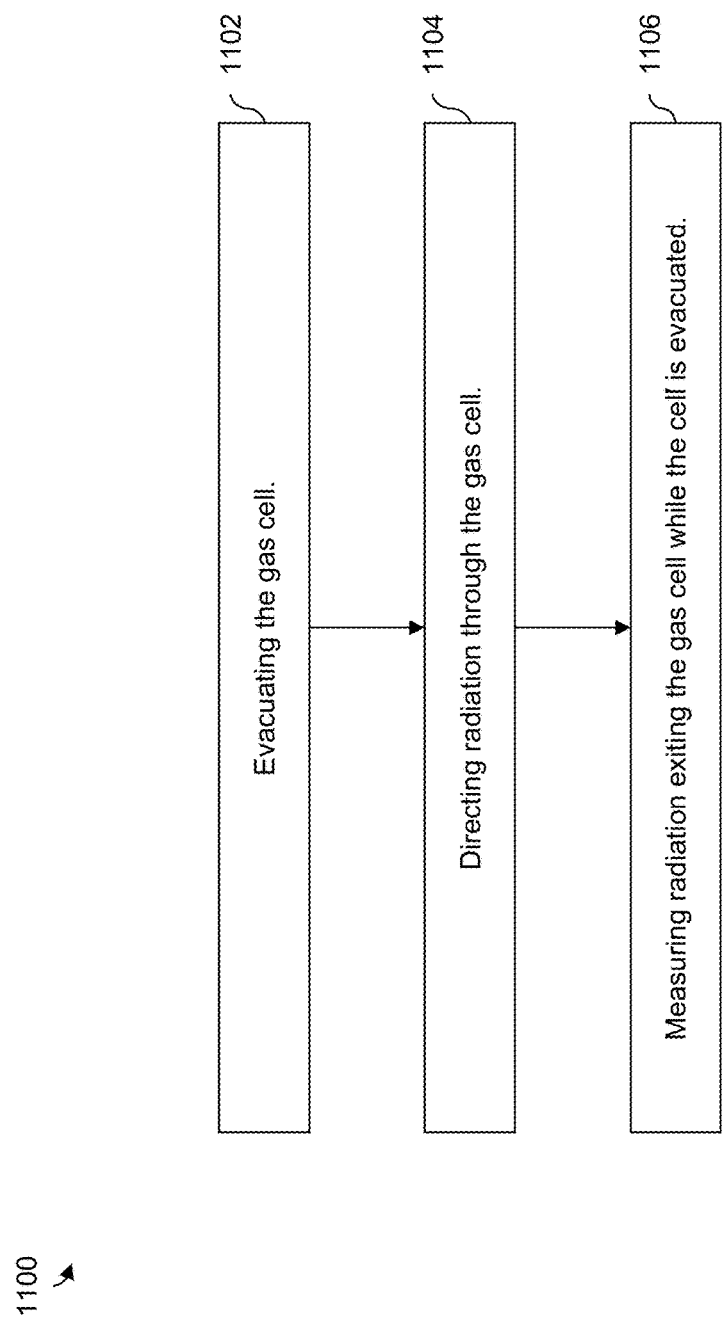
FIG. 11 is a flowchart illustrating an exemplary method for calibrating the device for analyzing gas(es) of FIG. 3.

FIG. 11 is a flowchart illustrating an exemplary method 1100 for calibrating gas cell 62. Method 1100 may be incorporated into method 900 or may be conducted independently of method 900. Also, method 1100 may be combined with one or more steps of other methods disclosed herein. In various embodiments, method 1100 may be used to conduct a calibration of gas analyzer 34 prior to conducting FTIR spectroscopy on the extracted gas(es). For example, method 1100 may comprise: evacuating gas cell 62 (see block 1102) and optionally creating a vacuum condition inside gas cell 62; directing radiation R through gas cell 62 (see block 1104); and measuring radiation exiting gas cell 62 while the cell is evacuated (see block 1106) and optionally under the vacuum condition. Method 1100 may further comprise analyzing gas cell 62 using FTIR spectroscopy so that the structure of gas cell 62 may be taken into account when FTIR spectroscopy of the extracted gas(es) is subsequently carried out. Accordingly, in various embodiments, method 1100 for calibrating as cell 62 may be carried out without the need for consumables or calibration gases.

For example, such calibration (e.g., method 1100) may be conducted before the receipt of extracted gas(es) into cavity 96 of gas cell 62. In various embodiments, calibration of gas analyzer 34 may comprise evacuating cavity 96 and acquiring measured data 90 (e.g., one or more signals representative of the absorbance by gas cell 62 at one or more wavelengths) while cavity 96 is under the vacuum condition. The vacuum condition need not be absolute vacuum but may comprise at least some differential pressure between cavity 96 and the atmosphere. In various embodiments, the vacuum condition may comprise a pressure inside cavity 96 being between about 3 kPa lower than the pressure of the atmosphere. In some embodiments, the vacuum condition may comprise a pressure inside cavity 96 being more than about 3 kPa lower than the pressure of the atmosphere. For example, in some applications, it may be desirable a pressure differential that is greater than about 3 kPa in order to reduce the risk of reference errors during calibration.

Accordingly, depending on the application the pressure differential achievable during the evacuation of cavity 96 may be at least 3 kPa.

Absorbance data obtained during the calibration procedure may be used to take into account the absorbance of gas cell 62 during FTIR spectroscopy. In various embodiments, the calibration procedure may comprise acquiring interferogram data of gas cell 62 when gas cell 62 is evacuated and the interferogram data may subsequently be converted to absorbance. The conversion of interferogram data to absorbance may be conducted according to known or other methods. For example, the conversion may be in accordance with one or more blocks and/or steps of method 1500 (described further below and illustrated in FIG. 15). During FTIR analysis, the absorbance data of the extracted gas(es) may be similarly derived from interferogram data acquired when the extracted gas(es) is/are permitted in gas cell 62 and then the absorbance data of the extracted gas(es) may be compared to compressed calibration data (e.g., absorbance of gas cell 62) by means of a least-squares regression for each of the gas constituents (e.g., hydrocarbons) of interest. Even though the calibration procedure is described in terms of absorbance data, other transformations or measurement modalities (e.g., emission, transmittance) of the FTIR spectrum may be used to obtain quantitative information about the gases from the measured data.

In various embodiments, the radiation directed through gas cell 62 in the various methods disclosed herein may comprise broadband radiation including wavelengths in the mid infrared range. Accordingly, method 1100 may comprise generating one or more signals representative of the absorbance of gas cell 62 at one or more wavelengths while gas cell 62 is under the vacuum condition.

The evacuation of gas cell 62 may be conducted by at least partially closing valve 58 and operating pump 60 in order to produce a vacuum condition inside of cavity 92. In various embodiments, valve 58 may be fully closed during at least part of the evacuation of gas cell 62. Pump 60 may be operated in order to maintain the vacuum condition when the radiation is directed through gas cell 62 and also when the radiation exiting the gas cell is being measured. Alternatively, pump 60 may be shut off once satisfactory evacuation of gas cell 62 has been achieved and the measuring of the radiation exiting gas cell 62 may be carried out while pump 60 is off and valve 58 is closed.

The methods disclosed herein may also comprise monitoring one or more temperatures and/or one or more pressures associated with gas cell 62. The temperature of the contents of gas cell 62 may be monitored via temperature sensor 82b and the pressure inside of cavity 92 of gas cell 62 may be monitored via pressure sensor 82a. Temperature and pressure data may be used during FTIR spectroscopy. For example, the wavelengths at which atomic transitions or other spectral characteristic(s) may occur may be dependent on the temperature and/or pressure inside cavity 92. Accordingly, temperature and/or pressure data may be used to take into account such environment factors during FTIR spectroscopy. For example, temperature and pressure data may be used to use applicable values within stored data 86 for comparison with measured data 90.

Figure 12:
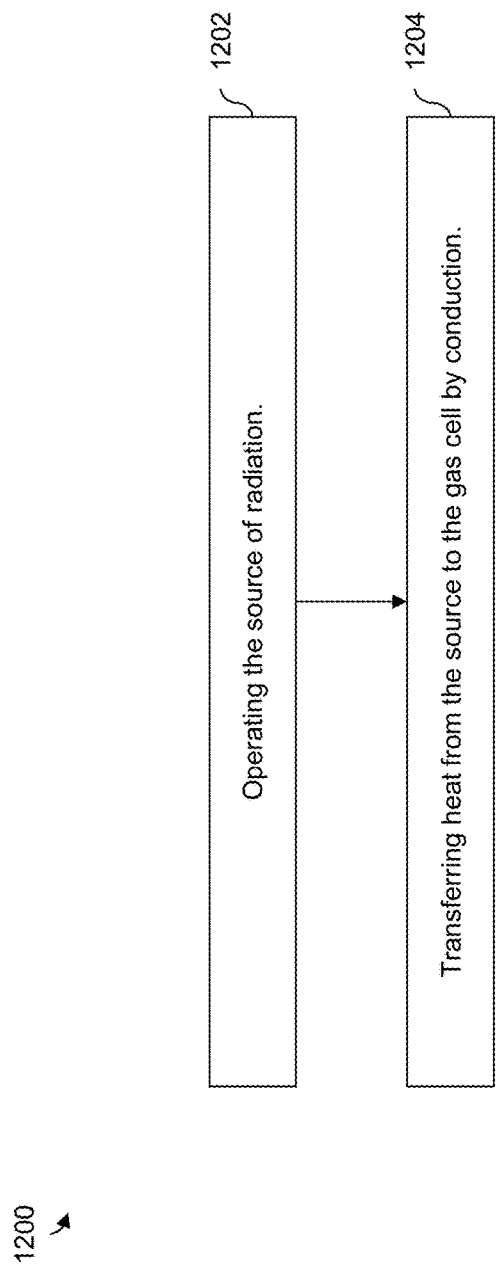
FIG. 12 is a flowchart illustrating an exemplary method for heating the gas cell of FIG. 8.

FIG. 12 is a flowchart illustrating an exemplary method 1200 for heating gas cell 62. Method 1200 may be incorporated into other methods disclosed herein or may be conducted independently of the other methods. Also, method 1200 may be combined with one or more steps of other methods disclosed herein. For example, method 1200 may be carried out during a start-up sequence of gas analyzer 34. As mentioned above, the spectral characteristics of interest during FTIR spectroscopy may be temperature-dependent and it may be desirable to maintain the temperature of the contents of cavity 92 within a predetermined range. Also, it may be desirable to maintain the temperature of gas cell 62 above a predetermined temperature in order to substantially prevent or reduce the risk of condensation of any part of extracted gas(es) to take place inside gas cell 62. For example, the temperature above which the temperature of gas cell 62 should be maintained may be based on an amount of moisture (i.e., water vapor) expected to be present the extracted gas(es).

Accordingly, it may be desirable to monitor at least one temperature associated with gas cell 62 and also actively control the temperature of (e.g., heat) gas cell 62. In various embodiments, gas cell 62 may be heated using any suitable known or other heating methods. For example, method 1200 may be used for heating gas cell 62 and may comprise: operating radiation source 64 (see block 1202); and transferring heat from radiation source 64 to gas cell 62 by conduction. For example, while radiation source 64 is directing radiation through gas cell 62, (waste) heat generated by radiation source 64 by virtue of its operation may be conducted to gas cell 62 via thermal conductor 84 (see FIG. 5). As explained above, radiation source 64 may be disposed relatively close to gas cell 62 so that heat may be conducted through thermal conductor 84 over a relatively short distance. Other forms of passive and/or active heating may also be carried out using other components inside of enclosure 44 of gas analyzer 34. For example, other forms of passive or active heating may include transferring heat from one or more components of a gas analyzer 34 to gas cell 62.

It should be understood that active control of the temperature of gas cell 62 may be done for reasons other than preventing or reducing condensation and may also be done using one or more heating means. For example, the active heating of gas cell 62 may be done using auxiliary heater 85. Alternatively or in addition, heating of gas cell 62 may be done using spare cycles of processor 78a of SBC 78 in order to generate heat inside enclosure 44 and thereby cause heating of gas cell 62. For example, processor 78a may be instructed to execute (e.g., otherwise meaningless) calculations/operations in order to cause the temperature of processor 78a, and consequently the temperature inside enclosure 44, to increase.

Another method of heating gas cell 62 that may be used in addition to or instead of those described herein is via the operation of pump 60 and valve 58. For example, while pump 60 is operating to draw extracted gas(es) into and then out of cavity 92, valve 58 may be operated to throttle the flow of extracted gas(es) through cavity 92. By reducing the flow rate of gas(es) through cavity 92 the heat loss due to the flow of relatively cooler gas(es) may also be reduced. In addition, the partial closing of valve 58 may also increase the load on pump 60 by increasing the resistance to flow through conduit 43 and thereby cause pump 60 to draw more current and generate more heat depending on the type of pump 60 used. The heat generated by pump 60 may cause the temperature inside of enclosure 44 to increase and consequently cause additional heat transfer to gas cell 62.

Figure 13:
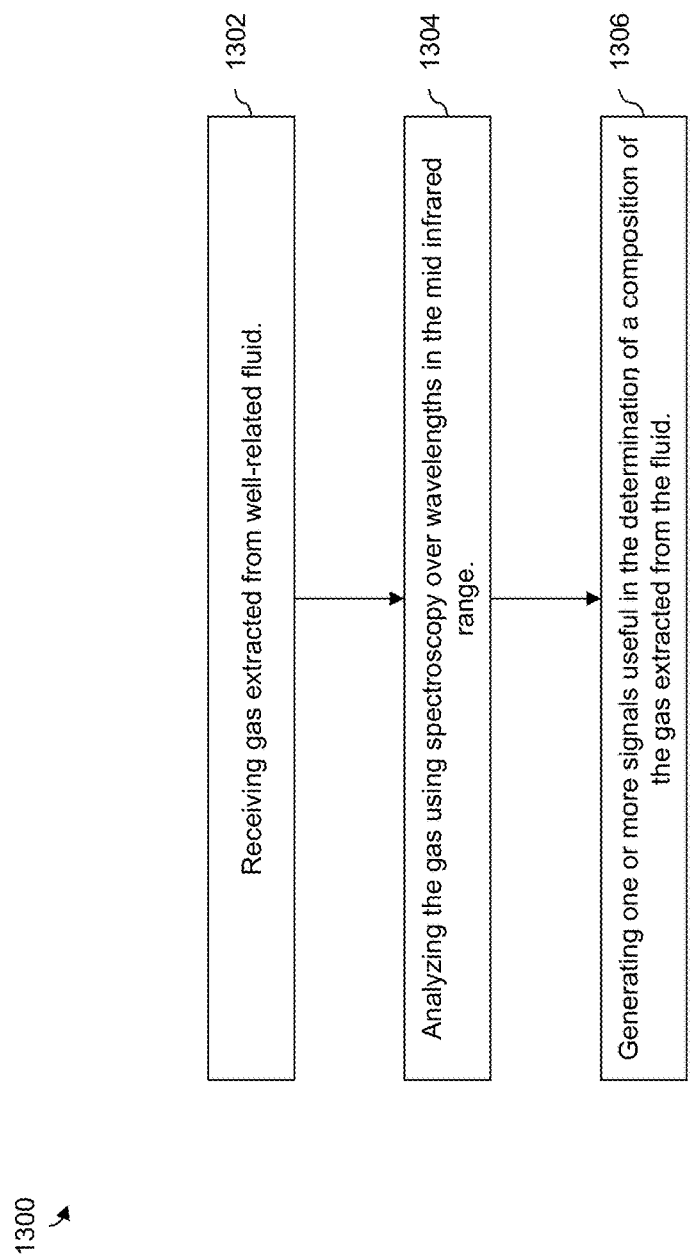
FIG. 13 is a flowchart illustrating another exemplary method for analyzing gas(es) extracted from well-related fluid.

FIG. 13 is a flowchart illustrating an exemplary method 1300 for online analysis of gas(es) extracted from a fluid associated with an ongoing well-related operation. Method 1300 may be conducted substantially in real-time while the well-related application is being carried out. Method 1300 may comprise: receiving gas(es) extracted from fluid such as drilling fluid 18 associated with the well-related operation (see block 1302); analyzing the gas using spectroscopy over wavelengths in the mid infrared range (see block 1304); and generating one or more signals useful in the determination of the composition of the gas(es) extracted from the fluid (see block 1306). Method 1300 may be incorporated into other methods disclosed herein or may be conducted independently of the other methods. Also, method 1300 may be combined with one or more steps of other methods disclosed herein. For example, method 1300 may comprise conducting spectroscopy over a range of wavelengths between about 5 μm and about 13.5 μm. Also, similarly to other methods disclosed herein, the analysis of the gas(es) may be conducted on a continuous flow of gas(es) extracted from drilling fluid 18. Also, the one or more signals generated may be representative of an absorbance of the gas(es) at one or more wavelengths.

Figure 14:
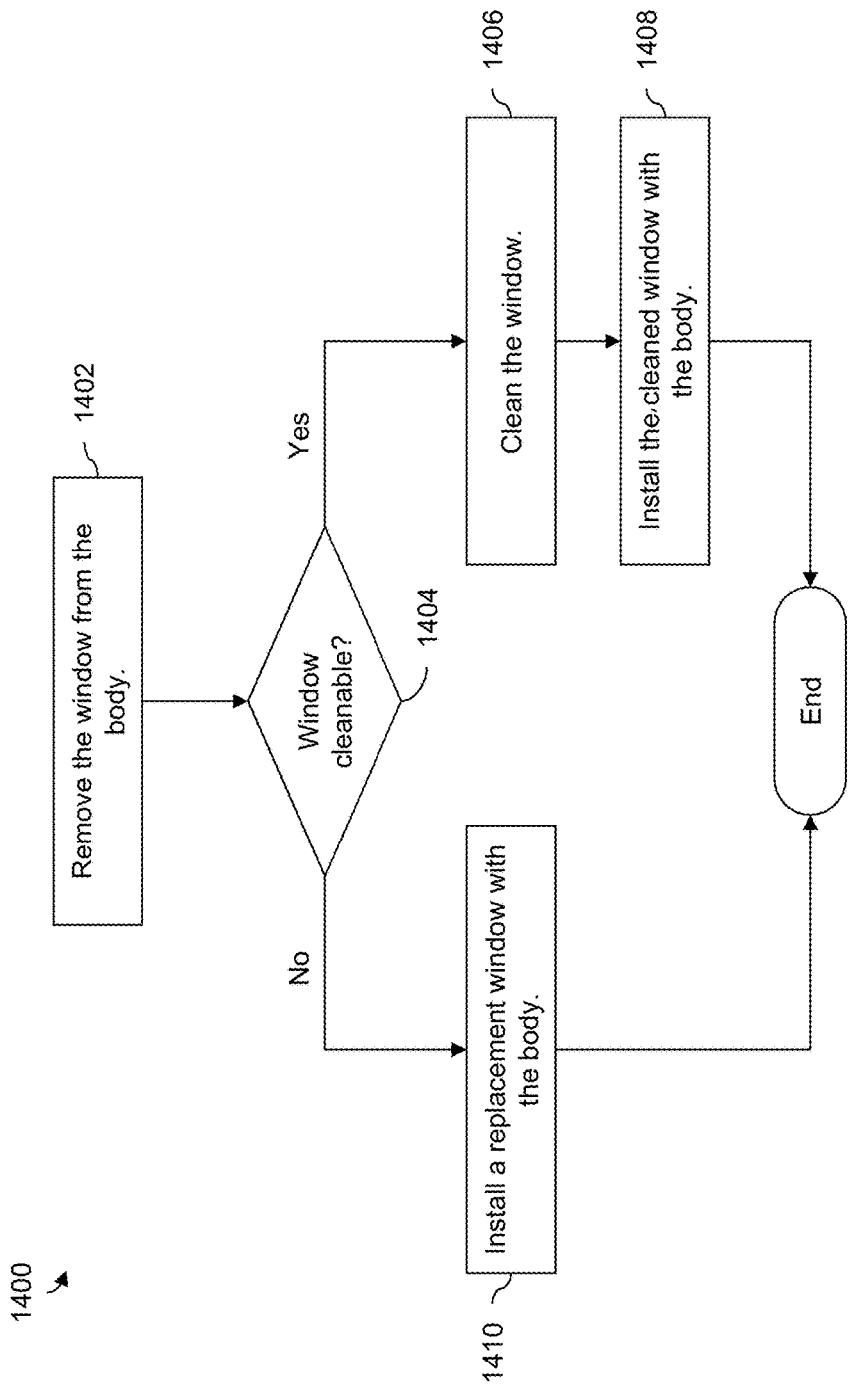
FIG. 14 is a flowchart illustrating an exemplary method for servicing the gas cell of FIG. 8.

FIG. 14 is a flowchart illustrating an exemplary method 1400 for servicing gas cell 62. As mentioned above, windows 98a, 98b may be removable from body 96 of gas cell 62 and may facilitate servicing of gas cell 62. Depending on the environmental conditions and the type of gas(es) flowing through gas cell 62, it may be desirable to clean portions of gas cell 62 to remove residue that may have collected inside of cavity 92 in order to prevent the accumulation of such residue from affecting FTIR spectroscopy. Method 1400 relates to a method for servicing gas cell 62 where the method may comprise removing one or more of windows 98a, 98b from body 96 (see block 1402). Depending on the type of windows 98a, 98b, the one or more windows 98a, 98b may be cleanable. If, at decision block 1404, the one or more windows 98a, 98b are determined to be cleanable, the one or more windows 98a, 98b may be cleaned (see block 1406) and then re-installed with body 96 (see block 1408). If, at decision block 1404, the one or more windows 98a, 98b are determined not to be cleanable, one or more replacement windows may be obtained and installed with body 96 (see block 1410). In various embodiments, the one or more removable windows 98a, 98b may include two or more removable windows 98a, 98b.

Method 1400 may also comprise cleaning cavity 92 while one or more of windows 98a, 98b have been removed. The cleaning of windows 98a, 98b and or cavity 92 may be conducted using known or other methods suitable for cleaning optical components and/or gas handling equipment. The re-installation of the one or more cleaned windows 98a, 98b with body 96 may include establishing a substantially hermetic seal between each of the one or more cleaned windows and body 96. Similarly, the installation of the one or more replacement windows with body 96 may include establishing a substantially hermetic seal between each of the one or more replacement windows and body 96.

Figure 15:
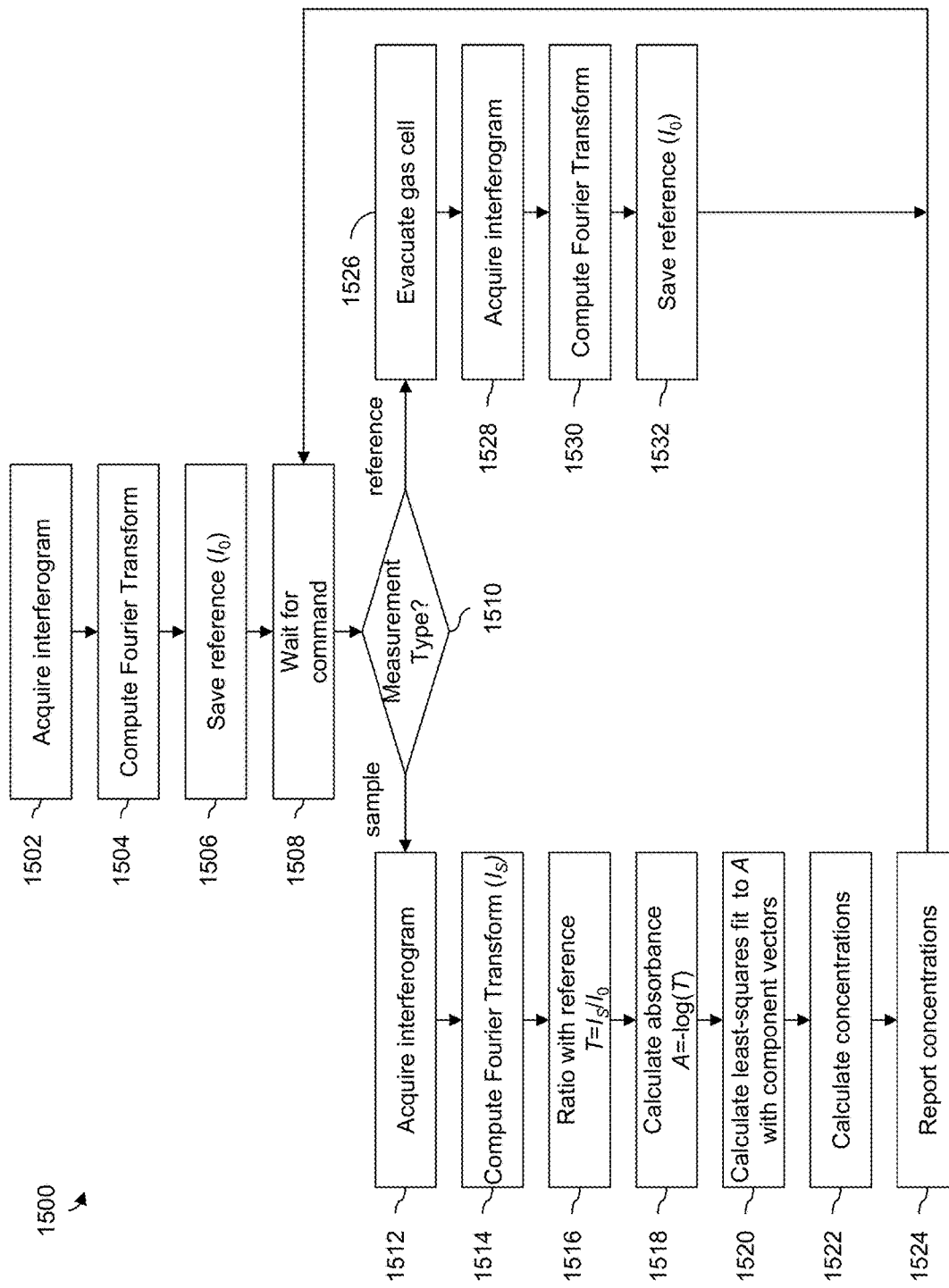
FIG. 15 is a flowchart illustrating an exemplary method that may be conducted by the device for analyzing gas(es) of FIG. 3.

FIG. 15 is a flowchart illustrating an exemplary method 1500 that may be conducted by gas analyzer 34. Method 1500 may be carried out in real-time while one or more well-related operations are also being conducted. Method 1500 may comprise calibration procedures and gas analysis methods described above. Accordingly, method 1500 or part(s) thereof may be incorporated into other methods disclosed herein or may be conducted independently of the other methods. Also, method 1500 or part(s) thereof may be combined with one or more steps of other methods disclosed herein. For example method 1500 may initially comprise obtaining calibration data as described above in order to acquire intensity/absorption data associated with gas cell 62 prior to conducting analysis on the extracted gas(es). For example, method 1500 may comprise method 1100 described above or one or more parts thereof. Accordingly, method 1500 may comprise: acquiring a reference interferogram (see block 1502); computing the Fourier Transform of the reference interferogram to obtain reference intensity data for each wavelength (see block 1504); saving the reference intensity data $I_0$ (e.g., in memory 78b) (see block 1506) and waiting for further instructions (see block 1508). In various embodiments, further instructions may be provided to gas analyzer 34 via modem 80 or in the form of machine-readable instructions already stored in memory 78b. The further instructions may comprise instructions relating to the type of measurements to be conducted using gas analyzer 34. Depending on the type of measurement(s) commanded, method 1500 may take different courses of action at decision block 1510 as described below.

Conditioned upon the measurement type commanded being "sample", this may be indicative that the measurement to be taken is that of the extracted gas(es) in gas cell 62 while a continuous flow of extracted gas(es) is flowing through gas cell 62. Accordingly, method 1500 may further comprise: acquiring a sample interferogram when the gas(es) is/are flowing through gas cell 62 (see block 1512); computing the Fourier Transform of the sample interferogram to obtain sample intensity data $I_s$ for each wavelength (see block 1514); obtaining a ratio (i.e., transmissivity T) of the sample intensity data over the reference intensity data $I_0$ (see block 1516); calculating absorbance (see block 1518) (the logarithm of the transmissivity T at each wavelength is related to the volume fraction of each gas that is present according to the Beer-Lambert relation); calculating the least-squares fit to the absorbance with component vectors (see block 1522); calculating concentrations of one of more constituents of the gas(es) in gas cell 62 (see block 1522); and reporting the calculated concentrations (see block 1524). The reporting of the calculated concentrations may be done wirelessly via modem 80.

Conditioned upon the measurement type commanded being "reference", this may be indicative that the measurement to be taken is a reference intensity/absorption measurement associated with gas cell 62. Accordingly, method may further comprise: acquiring a reference interferogram (see block 1526); computing the Fourier Transform of the reference interferogram to obtain reference intensity/absorption data for each wavelength (see block 1528); and saving the reference data (e.g., in memory 78b) (see block 1532) and returning to block 1508 to wait for further instructions. The reference intensity/absorption data may be used during subsequent analysis of gas(es) in gas cell 62.

In various embodiments, the flow through gas cell 62 may, for example, allow for a full exchange of gas in about 1 second and may substantially match the time required to conduct the analysis of the gas(es) in gas cell 62. For example, the flow rate of gas through gas cell 62 may be selected to provide a full exchange of gas(es) through cavity 92 of gas cell 62 within a period of time substantially corresponding to the time required to carry out blocks 1512, 1514, 1516, 1518, 1520 and 1522. It should be understood that the time intervals between measurements and also between full exchanges of gas(es) through gas cell 62 may vary based on different requirements of specific applications.

Figure 16:
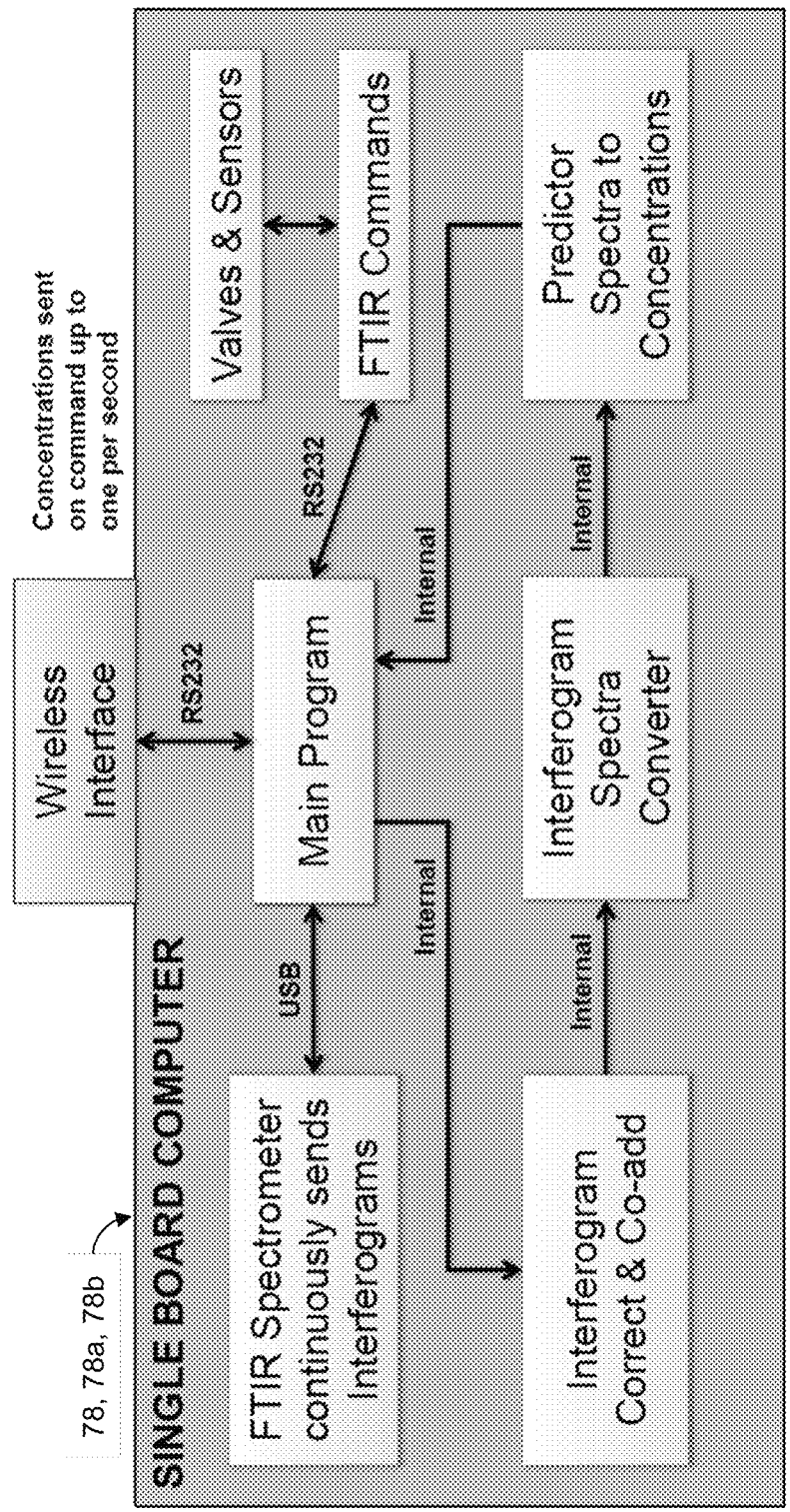
FIG. 16 shows a schematic diagram of exemplary software interfaces associated with the data processing device of FIG. 6.

FIG. 16 shows a schematic diagram of exemplary software interfaces associated with SBC 78. As explained above, SBC 78 may be configured to control at least some aspects of operation of gas analyzer 34. The control function(s) performed by SBC 78 may be in accordance with machine-readable instructions stored in memory 78b and/or received via modem 80 (e.g., wireless interface). For example, SBC 78 may comprise a main program stored thereon (e.g., in memory 78*b*) together with one or more sub programs that may handle more specific tasks. SBC 78 may also communicated with other components of gas analyzer 34. For example, SBC 78 may communicated with FTIR electronics 74 via a Universal Serial Bus (USB), RS-232 and/or other type of data communication link to send high-level commands to FTIR electronics 74, receive feedback about the operation of FTIR electronics 74 and/or also receive raw intensity/absorption data from FTIR electronics 74. SBC 78 may also directly or indirectly control the operation of and/or receive signals from valve 58, pump 60 and sensors 82 via, for example, an RS-232 or other data communication link. Various data processing functions using raw intensity/absorption data may be carried out internally within SBC 78 and/or may be conducted by another data processing device external to SCB 78. For example, as explained above concentrations of the constituents of extracted gas(es) may be computed by SBC 78 and transmitted wirelessly via modem 80 and/or data at various stages of processing (including raw data) may be transmitted wireless via modem 80.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified. The present disclosure may be embodied in other specific forms without departing from the subject matter of the claims. Also, one skilled in the relevant arts will appreciate that while the systems, devices and assemblies disclosed and shown herein may comprise a specific number of elements/components, the systems, devices and assemblies could be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

What is claimed is:

1. A method for real-time analysis of gas extracted from a fluid associated with an ongoing well-related operation, the method comprising:
    calibrating a device used to analyze the gas extracted from the fluid associated with the well-related operation where the calibration comprises:
        evacuating a gas cell of the device using a pump disposed downstream of the gas cell while a valve disposed upstream of the gas cell is closed, to produce a vacuum condition inside the gas cell; and
        acquiring a signal representative of the absorbance of the gas cell at one or more wavelengths while the cell is under the vacuum condition;
    after calibrating the device, drawing the gas extracted from the fluid associated with the well-related operation into the gas cell using the pump disposed downstream of the gas cell while the valve disposed upstream of the gas cell is open;
    analyzing the gas in the gas cell using Fourier Transform Infrared (FTIR) spectroscopy taking into account the absorbance of the gas cell and
    generating one or more signals useful in the determination of a composition of the gas extracted from the fluid.

2. The method as defined in claim 1, comprising transmitting the one or more signals wirelessly.

3. The method as defined in claim 1, wherein the analysis is conducted on a continuous flow of the gas.

4. The method as defined in claim 3, wherein the continuous flow of the gas is a substantially laminar flow.

5. The method as defined in claim 1, wherein the one or more signals useful in the determination of the composition of the gas extracted from the fluid are representative of the absorbance of the gas at one or more wavelengths.

6. The method as defined in claim 1, comprising monitoring a temperature associated with the gas cell into which the gas is drawn for analysis.

7. The method as defined in claim 1, comprising monitoring a pressure associated with the gas cell into which the gas is drawn for analysis.

8. The method as defined in claim 6, comprising heating the gas cell by conducting heat from a source of radiation to the gas cell.

9. The method as defined in claim 6, comprising transferring heat from one or more components of a device used to analyze the gas to the gas cell.

10. The method as defined in claim 6, comprising maintaining at least one condition of the gas cell to substantially prevent condensation of at least a portion of the gas expected to be drawn in the gas cell.

11. The method as defined in claim 6, comprising controlling a temperature associated with the gas cell to substantially prevent condensation of at least a portion of the gas expected to be drawn in the gas cell.

12. The method as defined in claim 11, comprising using spare cycles of a data processor to generate heat inside an enclosure housing the gas cell.

13. The method as defined in claim 11, comprising at least partially closing the valve to the gas cell while maintaining the operation of a pump for drawing the gas into the gas cell.

14. The method as defined in claim 11, comprising activating an auxiliary heater to heat the gas cell.

15. The method as defined in claim 1, wherein the FTIR spectroscopy is conducted using wavelengths between 5 μm and 13.5 μm.

16. A system comprising:
    a reservoir configured to hold a fluid associated with a well-related operation;
    a gas extractor configured to cause the release of gas from the fluid in the reservoir; and
    a device configured to conduct Fourier Transform Infrared (FTIR) spectroscopy on the extracted gas, the device comprising: an inlet in fluid communication with the gas extractor; a gas cell in communication with the inlet via a valve; and a pump disposed downstream of the gas cell for drawing the gas from the inlet into the gas cell.

17. The system as defined in claim 16, wherein the device is configured to conduct FTIR spectroscopy using wavelengths between 5 μm and 13.5 μm.

* * * * *